(12) United States Patent
Trivedi et al.

(10) Patent No.: US 10,596,115 B2
(45) Date of Patent: Mar. 24, 2020

(54) PHARMACEUTICAL COMPOSITION FOR THE TREATMENT OF DIMINUTION OF BONE TISSUE

(71) Applicant: Council of Scientific & Industrial Research, New Delhi (IN)

(72) Inventors: Ritu Trivedi, Lucknow (IN); Prabhat Ranjan Mishra, Lucknow (IN); Divya Singh, Lucknow (IN); Vikram Khedgikar, Lucknow (IN); Priyanka Kushwaha, Lucknow (IN); Sulekha Adhikary, Lucknow (IN); Dharmendra Choudhary, Lucknow (IN); Jyoti Gautam, Lucknow (IN); Avinash Kumar, Lucknow (IN); Anirudha Karvande, Lucknow (IN); Ashwni Verma, Lucknow (IN); Shweta Sharma, Lucknow (IN); Prabodh K Trivedi, Lucknow (IN); Neelam S. Sangwan, Lucknow (IN); Rajender S. Sangwan, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/904,981

(22) PCT Filed: Jul. 16, 2014

(86) PCT No.: PCT/IN2014/000475
§ 371 (c)(1),
(2) Date: Jan. 14, 2016

(87) PCT Pub. No.: WO2015/008301
PCT Pub. Date: Jan. 22, 2015

(65) Prior Publication Data
US 2016/0158152 A1    Jun. 9, 2016

(30) Foreign Application Priority Data
Jul. 17, 2013  (IN) ............................ 2145/DEL/2013

(51) Int. Cl.
| | | |
|---|---|---|
| *A61K 9/127* | (2006.01) | |
| *A61K 8/14* | (2006.01) | |
| *A61K 8/11* | (2006.01) | |
| *A61K 31/00* | (2006.01) | |
| *A61K 47/26* | (2006.01) | |
| *A61K 47/36* | (2006.01) | |
| *A61K 31/585* | (2006.01) | |

(52) U.S. Cl.
CPC ............ *A61K 9/127* (2013.01); *A61K 31/585* (2013.01); *A61K 47/26* (2013.01); *A61K 47/36* (2013.01)

(58) Field of Classification Search
CPC . A61K 9/127; A61K 8/14; A61K 8/11; A61K 31/00; A61P 19/10
See application file for complete search history.

(56) References Cited

U.S. PATENT DOCUMENTS

| 4,636,381 A * | 1/1987 | Takada .................... A61K 9/127 424/450 |
| 5,043,165 A | 8/1991 | Radhakrishnan |
| 5,494,668 A | 2/1996 | Patwardhan |
| 5,776,486 A * | 7/1998 | Castor ................... A61K 9/1277 264/4.1 |
| 2004/0197393 A1* | 10/2004 | Smyth-Templeton ...................... A61K 9/1272 424/450 |
| 2007/0122497 A1 | 5/2007 | Managoli |
| 2009/0285882 A1* | 11/2009 | Weiss ...................... A01N 25/26 424/450 |
| 2011/0230551 A1* | 9/2011 | Gunatilaka .......... A61K 31/366 514/460 |
| 2012/0053331 A1 | 3/2012 | Huh et al. |
| 2013/0071321 A1* | 3/2013 | Low ....................... A61K 51/10 424/1.21 |

FOREIGN PATENT DOCUMENTS

| EP | 2735314 A1 * | 5/2014 | ......... A61K 31/7088 |
| WO | WO-8905151 A1 * | 6/1989 | ............. A61K 9/127 |
| WO | WO 9932089 A1 * | 7/1999 | ........... A61K 9/1075 |
| WO | 2010053655 | 5/2010 | |
| WO | WO 2011064558 A2 * | 6/2011 | ........... A61K 9/0019 |

OTHER PUBLICATIONS

Drug Development & Delivery. Chitosan: A Unique Pharmaceutical Excipient. Mar. 27, 2008. vol. 6. No. 6. <http://drug-dev.com/Main/Back-Issues/Chitosan-A-Unique-Pharmaceutical-Excipient-205.aspx>.*
Njeh et al. Bone loss: Quantitative imaging techniques for assessing bone mass in rheumatoid arthritis. Arthritis Research & Therapy. Aug. 3, 2000. 2:446.*
Manconi et al. Improving Oral Bioavailability and Pharmacokinetics of Liposomal Metformin by Glycerolphosphate-Chitosan Microcomplexation. Aaps PharmSciTech. Jun. 2013. 14(2): 485-496.*
Nagareddy et al. Withania somnifera improves bone calcification in calcium-deficient ovariectomized rats. (2006). Journal of Pharmacy and Pharmacology. 58:513-519. (Year: 2006).*
Khatri et al. Surface modified liposomes for nasal delivery of DNA vaccine. Mar. 17, 2008. Vaccine. vol. 26. pp. 2225-2233. (Year: 2008).*

(Continued)

*Primary Examiner* — Tracy Liu
(74) *Attorney, Agent, or Firm* — Dinsmore & Shohl, LLP

(57) ABSTRACT

A method for prevention and/or treatment of diminution of bone tissue using a composition comprising a compound selected from Withaferin A (WFA), Withanolide A, and Withanone. The composition showed enhanced WFA bioavailability in rodents against plain WFA, promotes bone marrow cell differentiation, and increases the percent of bone volume to tissue volume (BV/TV %) by 3 folds as compared to free Withaferin A (WFA).

11 Claims, 11 Drawing Sheets

(56) References Cited

OTHER PUBLICATIONS

Figure 1I:
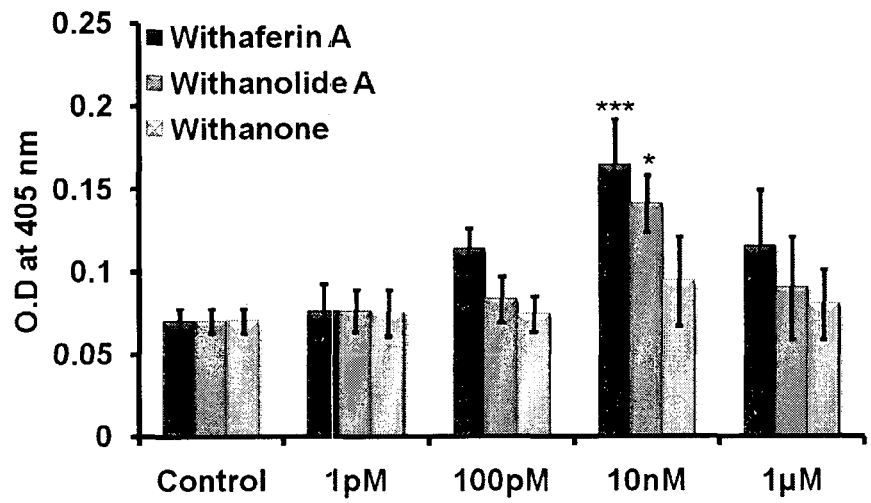

J. Filipović-Grčić, N. Škalko-Basnet & I. Jalšienjak (2001) Mucoadhesive chitosan-coated liposomes: characteristics and stability, Journal of Microencapsulation, 18:1, 3-12, DOI: 10.1080/026520401750038557 (Year: 2008).*

Lee et al. Effects of Chitosan Coating for Liposomes as an Oral Carrier. J. Exp. Biomed. Sci. (2011). vol. 17. Issue 3. pp. 211-216. (Year: 2011).*

International Search Report for International Application No. PCT/IN2014/000475, dated Dec. 19, 2014.

Written Opinion for International Application No. PCT/IN2014/000475, dated Jul. 14, 2015.

International Preliminary Report for International Application No. PCT/IN2014/000475, dated Oct. 21, 2015.

Database WPI; May 4, 2012; Week 201236; Thomson Scientific; London, GB.

Database WPI; Apr. 26, 2013; Week 201347; Thomson Scientific; London, GB.

Ichikawa, H., et al.; Withanolides potentiate apoptosis, inhibit invasion, and abolish osteoclastogenesis through suppression of nuclear factor-kB (NF-kB) activation and NF-kB—regulated gene expression; Molecular Cancer Therapeutics; Jun. 2006; pp. 1434-1445; vol. 5, No. 6; American Association for Cancer Research.

Khedgikar, V., et al.; Withaferin A: a proteasomal inhibitor promotes healing after injury and exerts anabolic effect on osteoporotic bone; Citation: Cell Death and Disease; Aug. 2013; pp. 1-17; vol. 4, No. 8; Macmillan Publishers Limited.

Garrett, I. R. et al., Selective inhibitors of the osteoblast proteasome stimulate bone formation in vivo and in vitro, The Journal of Clinical Investigation, Jun. 2003, pp. 1771-1782, vol. 111, No. 11.

Moallem, U. et al., Production performance and pattern of milk fat depression of high-yielding dairy cows supplemented with encapsulated conjugated linoleic acid, Animal, 2010, pp. 641-652, vol. 4., Issue 4.

Giuliani, Nicola et al., The proteasome inhibitor bortezomib affects osteoblast differentiation in vitro and in vivo in multiple myeloma patients, Blood, Jul. 1, 2007, pp. 334-338, vol. 110, No. 1.

Shapovalov, Yuriy et al., Proteasome inhibition with bortezomib suppresses growth and induces apoptosis in Dsteosarcoma, International Journal of Cancer, 2010, pp. 67-76, vol. 127.

Pennisi, Angela et al., The proteasome inhibitor, bortezomib suppresses primary myeloma and stimulates bone formation in myelomatous and nonmyelomatous bones in vivo, American Journal of Hematology, 2009. pp. 6-14, vol. 84.

Mirjalili, Mohammad 1-10SSEIN et al., Steroidal lactones from Withania somnifera, and ancient plant for novel medicine, Molecules, Jul. 3, 2009, pp. 2373-2393, vol. 14.

Gupta, Parul et al., Cloning and characterization of 2-C-methyl-D-erythritol-4-phosphate pathway genes for isoprenoid biosynthesis from Indian ginseng, Withania somnifera, Protoplasma, Apr. 15, 2012 (online), 11 pp.

Grover, Abhinav et al., Inhibition of the NEMO/IKKβ association complex formation, a novel mechanism associated with the NF-κb activation suppression by Withania somnifera's key metabolite witharferin A, BMC Genomics, 2010, 11 pp., vol., 11 (Suppl 4).

Matsuda, Hisashi et al., Structures of withanosides, I, II, III, IV, V,VI, and VII, New withanolide glycosides, from the roots of Indian Withania somnifera DUNAL. and inhibitory activity for tachyphylaxis to clonidine in isolated guinea-pig ileum, Bioorganic & Medicinal Chemistry, 2001, pp. 1499-1507, vol. 9.

Rasool, Mahaboobkhan et al., Suppressive effect of Withania somnifera root powder on experimental gouty arthritis: an in vivo and in vitro study, Chemico-Biological Interactions, 2006, pp. 174-180, vol. 164.

Mohan, Royce et al., Withaferin A is a potent inhibitor of angiogenesis, Angiogenesis, 2004, pp. 115-122, vol. 7.

Chaurasiya, Narayan Das et al., Analysis of withanolides in root and leaf of Withania somnifera by HPLC with photodiode array and evaporative light scattering detection, Phytochemical Analysis, 2008, pp. 148-154, vol. 19.

Yang, Huanjie et al., The tumor proteasome is a primary target for the natural anticancer compound withaferin A isolated from "Indian Winter Cherry", Molecular Pharmacology, 2007, pp. 426-437, vol. 71.

Sangwan, R. S. et al., Phytochemical variability in commercial herbal products and preparations of Withania somnifera (Ashwagandha), Current Science, Feb. 10, 2004, pp. 461-465, vol. 86, No. 3.

Elliott, Peter J. et al., A new target for novel drug therapies, American Journal of Clinical Pathologists, 2001, pp. 637-646, vol. 116.

Simovic et al., "Nanoparticle layers controlling drug release from emulsions", European Journal of Pharmaceutics and Biopharmaceutics, vol. 67, 2007, pp. 39-47.

Yin et al., "Drug permeability and mucoadhesion properties of thiolated trimethyl chitosan nanoparticles in oral insulin delivery", Biomaterials, vol. 30, 2009, pp. 5691-5700.

Turjeman/Barenholz, "Liposomal nano-drug based on amphipathic weak acid steroid prodrugs for the treatment of inflammatory diseases", Journal of Drug Targeting, 24:9, 2016, pp. 805-820.

Yhee et al., Self-assembled glycol chitosan nanoparticles for disease-specific theranostics, Journal of Controlled Release, 193, 2014, pp. 202-213.

Knight et al., "Structure, depolymerization, and cytocompatibility evaluation of glycol chitosan", Journal of Biomedical Materials Research Part A, 2007, pp. 787-798.

Hsia et al., "Osteophyte formation after ACL rupture in mice is associated with joint restabilization and loss of range of motion", Journal Orthopedic Research Author Manuscript, 2018, pp. 1-19.

Khedgikar et al., "Withaferin A: a proteasomal inhibitor promotes healing after injury and exerts anabolic effect on osteoporotic bone", Cell Death and Disease, Nature Publishing Group, 2013, pp. 1-17.

* cited by examiner

Figure 11I:
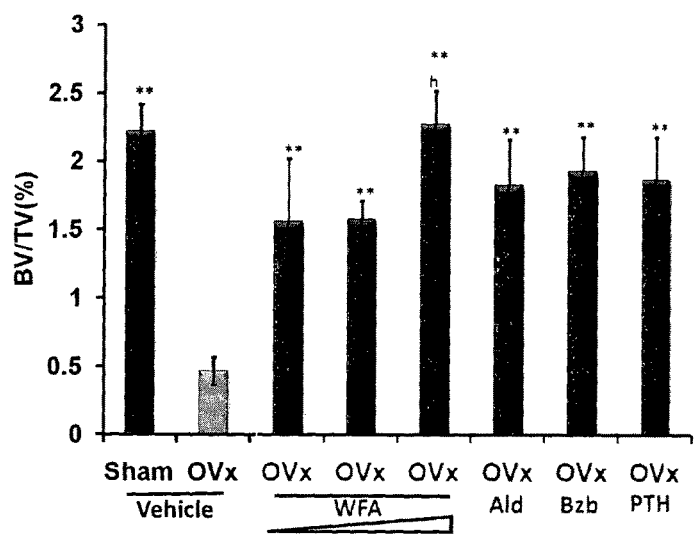
Figure 11:
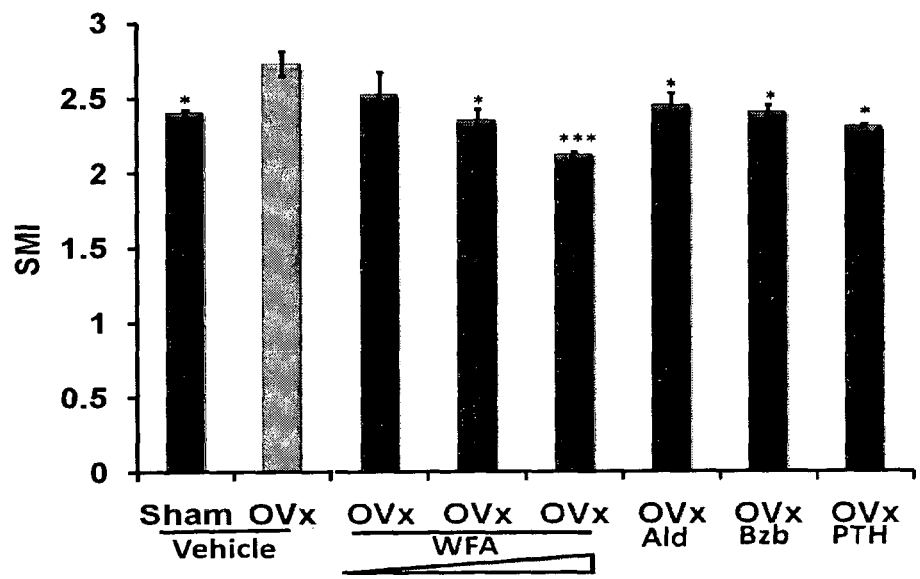

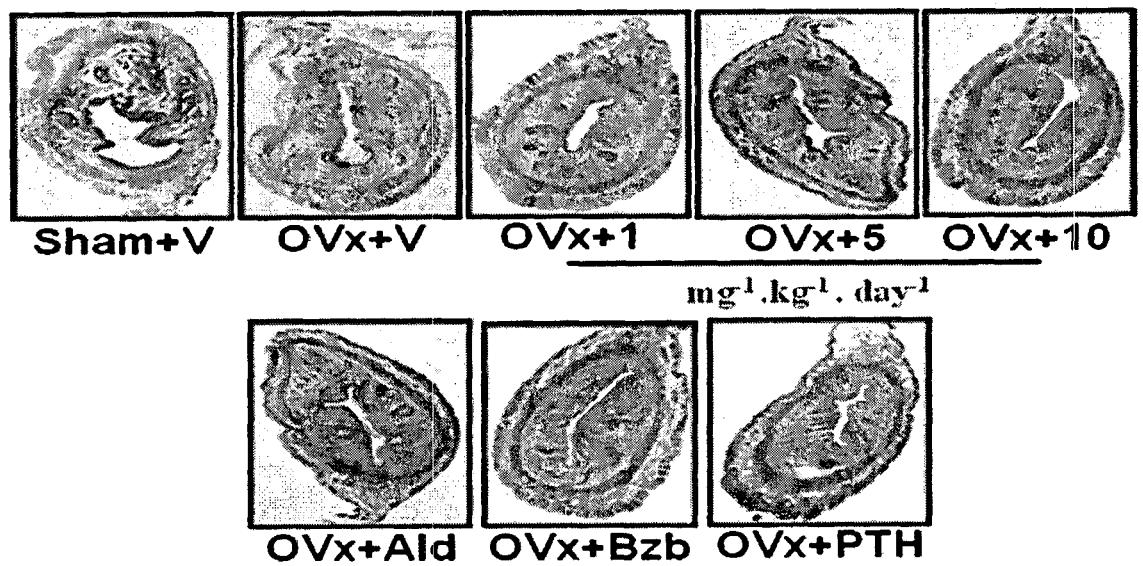
Fig. 11(iii)

PHARMACEUTICAL COMPOSITION FOR THE TREATMENT OF DIMINUTION OF BONE TISSUE

This application is a 35 U.S.C. 371 national stage filing and claims priority to PCT Application No. PCT/IN2014/000475, entitled "PHARMACEUTICAL COMPOSITION FOR THE TREATMENT OF DIMINUTION OF BONE TISSUE" filed on Jul. 16, 2014, which claims priority to Indian Application No. 2145/DEL/2013 filed on Jul. 17, 2013, both of which are incorporated by reference herein in their entirety.

FIELD OF THE INVENTION

The present invention relates to the proteasomal inhibitors useful in osteogenic activity and pharmaceutical composition thereof. The present invention also relates to the pharmaceutical composition that comprises of pure compound isolated from plants that are useful for the prevention and/or treatment of medical conditions associated with estrogen dependent or independent diseases or syndromes or disorders.

BACKGROUND OF THE INVENTION

*Withania somnifera* or Ashwagandha is a medicinal herb in Ayurveda. Though the extract and purified molecules (Withanolides) from this plant have been shown to have different pharmacological activities, their effect on bone formation has not been studied. Clinical and experimental research on various Proteasomal Inhibitors (PI's) revealed that inhibition of proteasome activity by PI's is critical for the activation of osteogenic transcription factors and bone metabolism (Garrett IR et al 2003, Yaccoby S et. al 2010). Further, preclinical studies on synthetic PI's like bortizomib (Bzb) show that it promotes osteoblastogenesis and suppresses osteoclastogenesis by regulating the ubiquitin proteasome dependent degradation of proteins and acts as an anti-myeloma agent (Giuliani N et. al 2007, Shapovalv Y et. al 2009, Pennisi et al 2009). However, no natural PI is reported to have enhanced osteogenic effect in vivo. *Withania somnifera* is one of the most ancient sought after herbs for the preparation of herbal formulations and dietary supplements (Mirjalili M H et al 2009, Gupta P et al 2013). In traditional Indian medicine or Ayurveda, the leaves and roots of *Withania* are prescribed to cure inflammation related disorders (Mirjalili M H et al 2009, Gupta P et al 2013). This plant has been studied extensively for its biologically active constituents, steroidal lactones and withanolides (Grover A et al 2010, Matsuda H et. al 2001). The health benefits of Ashwagandha are supported by clinical trials in case of inflammation and immune modulation and reduction of arthritis pain (Rasool M et. al 2006, Mohan R et. al 2004). Pharmacological studies suggest that major chemical constituents for medicinal activities are withanolides from this plant. To characterize the bioactive entities in Ashwagandha, several research groups investigated the chemical constituents by diverse analytical tools. The first compound of this group to be isolated was withaferin A (WFA), a highly oxygenated withanolide. It is one of the major and main biologically active constituent from this plant (Mirjalili M H et al 2009, Sangwan R S 2008 et al). Exploration of chemical structure reveals that aromatic ketone structure of WFA interacts with the hydroxyl group of the N-threonine of the β5 subunit and inhibits chymotrypsin-like activity of 20 S proteasome. In silico studies suggest that two conjugated ketone bonds in WFA make it more susceptible towards nucleophilic attack by β5 subunit of proteasome (Yang H et. al 2007, Grover A 2010). Both in vitro and in vivo evidences provide proteasomal chymotrypsin subunit as a novel molecular target of WFA. Despite these studies on pharmacological activities of WFA, their mechanism of action is not fully understood.

The present invention relates to Withanolides, the secondary metabolites present in several members of Solanaceae family, most prolifically in *Withania* species, particularly *Withania somnifera* (Sangwan et al. Current Science 461-465, 2004). Withanolides are $C_{28}$-steroidal lactones of triterpene ancestry, based on an intact or rearranged ergostane frame and chemically named as 22-hydroxy ergostane-26-oic acid 26,22-lactone. They are built on ergostane skeleton through appropriate oxidations at C-22 and C-26 to form a δ-lactone ring. Chemically or ergostanically, they are nomenclatured as 4, 27-dihydroxy-5β, 6β-epoxy-1-oxoWitha-2,24-dienolide, 4β, 20β-dihydroxy-5β, 6β-epoxy-1-oxo-Witha-2,24-dienolide, 5α, 20β-dihydroxy-6,7-α-epoxy-1-oxoWitha-2, 24-dienolide and 5α, 17α-dihydroxy-6, 7-α-epoxy-1-oxo-Witha-2, 24-dienolide, respectively.

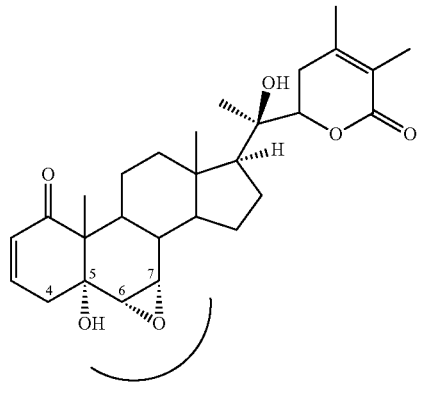

withanolide A withanone

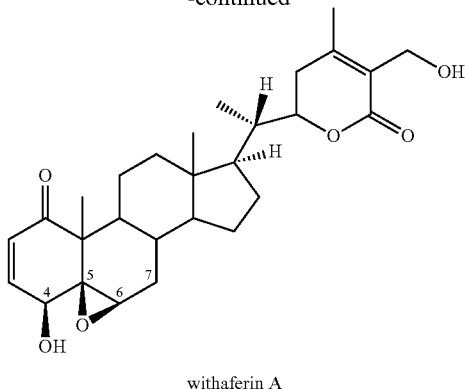

withaferin A

Proteasomal Inhibitors in Diseases

Studies show the role of proteasome and the potential uses of proteasomal inhibitors for the treatment of human diseases. Several natural and synthetic compounds that act as proteasome inhibitors have been reported (Garret I R et al 2003, Elliott P J et al 2001).

Proteasomes degrade damaged cellular proteins and various short lived regulatory proteins and govern a wide range of cellular functions. The expression of cell cycle stimulatory and inhibitory proteins has a major role in the development and progression of cancer. Proteasome inhibitors can stabilize many cell cycle inhibitory proteins and cause cell cycle arrest and apoptosis, thus limiting tumor development. It has been demonstrated that lactacystin (PI) significantly reduced angiogenesis suggesting that these compounds could be beneficial in disease states that rely on the formation of new blood vessels (Oikawa et. al 1998). PS-341 has been shown to limit the production of metastases and limit angiogenesis in several experimental cancer systems (Hideshima T et.al 2001, Elliott P J et al 2001). Thus, proteasome inhibitors show significant potential as anti-angiogenesis agents, influencing both inflammatory conditions and the development of cancer metastasis.

The proteasome is intimately linked to the production of the majority of the class I antigens. It is therefore conceivable that excessive inhibition of the proteasome might also increase the chance of viral infections. Schwartz O et al 1998 reported that replication of the HIV-1 virus could be limited by the degradative actions of the proteasome and that the proteasome inhibitor, MG-132 or lactacystin, enhanced the ability of the virus to replicate.

Through its regulation of NF-kappa B, the proteasome is central to the processing of many pro-inflammatory signals. Once released from its inhibitory complex through proteasome degradation of I kappa B, NF-kappa B induces the activation of numerous cytokines and cell adhesion molecules that orchestrate the inflammatory response (Alkalay I et al 1995).

The role of proteasome in bone formation appears to occur mainly through regulation factor Runx2/cbfa1 and additional components associated with bone morphogenetic proteins BMPs and Wnt signaling. These proteasomal effects on osteo-blastogenesis and on the production of osteo-clastogenic factors in osteogenic cells indirectly impact osteoclastogenesis but the proteasome is also directly involved in osteoclastogenesis because it controls important signaling pathways such as NFkB pathway, in osteoclast precursor cells (Yaccoby S 2010).

TABLE 1

List of proteasomal inhibitors (PI) at different stages of development

| | Source | Activity | Status | Reference |
|---|---|---|---|---|
| Natural (Bacterial) PI | | | | |
| Lactacystin | Streptomyces Sp. | Increases activity of Smads (in vitro) | Preliminary Pre-clinical stage | Ito y et al, 2011 |
| Epoxomicin | Actinomycetes strain no 996-17 | Increases bone volume and bone formation rate | Preliminary Pre-clinical stage | Mundy GR et al, 2005 |
| PSI | — | Increases bone volume and bone formation rate | Preliminary Pre-clinical stage | Mundy GR et al, 2005 |
| Synthetic PI | | | | |
| Bortezomib | synthetic | Osteogenic in vivo and in vitro both | FDA approved for MM treatment | N Giuliani et al, 2008 |
| MG-132 | synthetic | Stimulate bone | Preliminary | Garrett IR |

Sangwan et al. (US/2005.0266100 A1) discloses a process with improved isolation yields of Withaferin A, one of the Withanolides of *Withania somnifera*.

OBJECTS OF THE INVENTION

The main object of this invention is to provide a pharmaceutical composition comprising withaferin A for improved osteogenic action.

An object of the present invention is to provide a pharmaceutical composition comprising Withaferin A and Withanone for the treatment of osteoporosis.

Another object of the present invention is to provide a pharmaceutical composition comprising pure compound (withaferin A) isolated from plants that is useful for the prevention and/or treatment of various medical conditions associated with estrogen dependent or independent diseases or syndromes.

Yet another object of the invention is to provide a pharmaceutically acceptable withaferin A composition.

An object of the present invention is to provide a pharmaceutical composition comprising withaferin A which may be administered orally.

Still another object of the present invention is to provide a prevention and/or treatment of diminution of bones in humans and animals, and achievement of peak bone mass during skeletal growth.

SUMMARY OF THE INVENTION

Accordingly the present invention provides a pharmaceutical composition for prevention and treatment of diminution of bone comprising: a compound selected from the group consisting of Withaferin A (WFA), Withanolide A, and Withanone, and pharmaceutically acceptable excipients selected from the group comprising lipids, and polymers.

In another embodiment of the invention, wherein the composition additionally comprises a non-ionic surfactant.

In an embodiment of the invention wherein the Withaferin A (WFA), Withanolide A, and-Withanone are obtained from *Withania somnifera*.

In another embodiment of the invention wherein the concentration of Withaferin A (WFA), Withanolide, or Withanone is in the range of 0.1 to 0.5% w/v.

In an embodiment of the invention wherein the lipids are selected from the group consisting of soya phosphatidylcholine, di-stearoyl phosphatidylcholine, di-stearoylphosphatidyl glycerol, and cholesterol.

In yet another embodiment of the invention wherein the non-ionic surfactants are selected from the group consisting of Tween-20, Tween-40, Tween-60, Tween-80, Span 40, Span 60, Span 80, and Cremophor.

In still another embodiment of the invention wherein the polymers are chitosan or derivatives thereof selected from the group consisting of glycol chitosan and trimethyl chitosan.

In yet another embodiment of the invention wherein the composition is in the form of an oral formulation, powder, suspension, syrup, capsule, tablet, coated tablet, granule, controlled release formulation, cream, ointment, gel, emulsion, or solution for injection.

In still another embodiment of the invention wherein the composition is useful in bone healing, assisting bone regeneration, increasing bone mineral density, increasing bone growth, decreasing bone loss, and treating dimunition of bone tissue.

In yet another embodiment of the invention wherein the diminution of bone tissue occurs due to osteoporosis, estrogen loss, aging, arthritis, or drug induction.

In a further embodiment of the invention wherein the composition is useful for bone growth in children.

In an embodiment of the invention wherein the composition does not possess any uterine estrogenicity.

In an embodiment of the invention wherein the composition exhibits proteasomal activity to prevent diminution of bone tissue.

The present invention also provides a method of treating diminution of bone tissue wherein the method comprises administering to a subject a therapeutically effective amount of the pharmaceutical composition disclosed in the present application.

In an embodiment of the invention wherein the pharmaceutical composition is administered by oral, intravenous, intramuscular, or subcutaneous route.

In yet another embodiment of the invention wherein method comprises administering the composition disclosed in the present application for prophylaxis of age related osteoporosis in pets and humans, alleviation or prevention of bone disorder or maintenance of bone health.

In an embodiment of the invention wherein the method comprises administering the composition disclosed in the present application that increases percent of bone volume to tissue volume (% BV/TV) of femur, tibia and vertebrae by 3 fold as compared to free Withaferin A (WFA).

In still another embodiment of the invention wherein the composition comprises Withaferin A (0.1 to 0.5% w/v), polymer glycol chitosan (0.1 to 0.5% w/v), distearoyl phosphatidylcholine (DSPC), distearoyl phosphatidylglycerol (DSPG), or combination thereof, and Soya PC and cholesterol in the molar ratio of 7:3:3.

In an embodiment of the invention wherein the molar ratio of distearoyl phosphatidylcholine (DSPC) and distearoyl phosphatidylglycerol (DSPG) is in the range of 4-7.

Accordingly the present invention provides a process for preparation of a pharmaceutical composition, wherein the process comprises:
(i) preparing a solution of a compound selected from the group consisting of Withaferin A, Withanolide A, and Withanone, and lipids in a solvent followed by evaporation of solvent under reduced pressure to form a thin film;
(ii) keeping the film obtained in step (i) under vacuum up to 12 hrs and hydrating the film with PBS buffer at a pH in the range of 7.2 to 7.4 to obtain multilayered lipid vesicles;
(iii) sequentially extruding the multilayered lipid vesicles obtained in step (ii) through 400 nm, 200 nm, and 100 nm filter for 15 cycles to obtain a uniform population of vesicles;
(iv) coating the uniform population of vesicles of step (iii) with 0.1 to 0.5% w/v glycol chitoson (GC) to obtain liposomes; and
(v) dispersing the liposomes of step (iv) for 10 min under stirring to obtain the pharmaceutical composition.

In yet another embodiment of the invention wherein the solvent of step (i) is selected from the group consisting of chloroform, ethanol, and mixture thereof.

BRIEF DESCRIPTION OF ACCOMPANYING DRAWINGS

Figure 1:
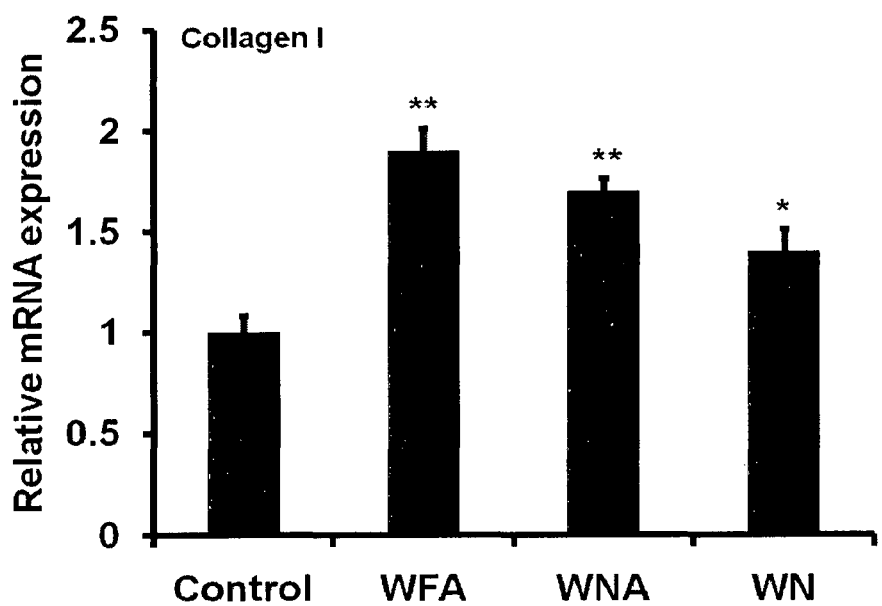

The present invention may be more clearly understood by reference to the following FIGS. 1-15):

FIG. 1: Withaferin A, Withanolide A and Withanone treatment to MCOs for 48 hours in osteoblast differentiation medium. WFA and Withanolide A show significantly increased ALP production compared with control. Values represent Mean±S. E of three independent experiments n=3. *$p<0.05$, ***$p<0.001$ compared with control. Similarly at 10 nM concentration WFA, Withanolide A and Withanone increases mRNA expression of collagen I [ii]. Values represent Mean±S. E of three independent experiments n=3. *$p<0.05$, $p<0.01$, *$p<0.001$ compared with control.

Figure 2:
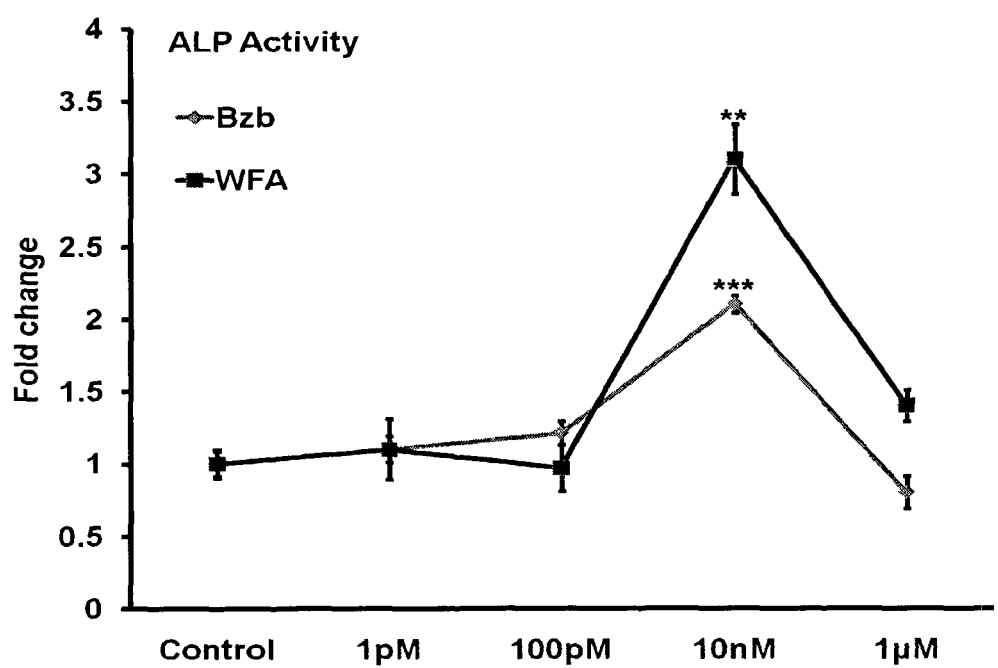

FIG. 2: WFA treatment of MCO's for 48 h in osteoblast differentiation medium significantly increased ALP production compared with control. Values represent Mean±S. E of three independent experiments (n=3). $p<0.01$, *$p<0.001$ compared with control vehicle group.

Figure 3:
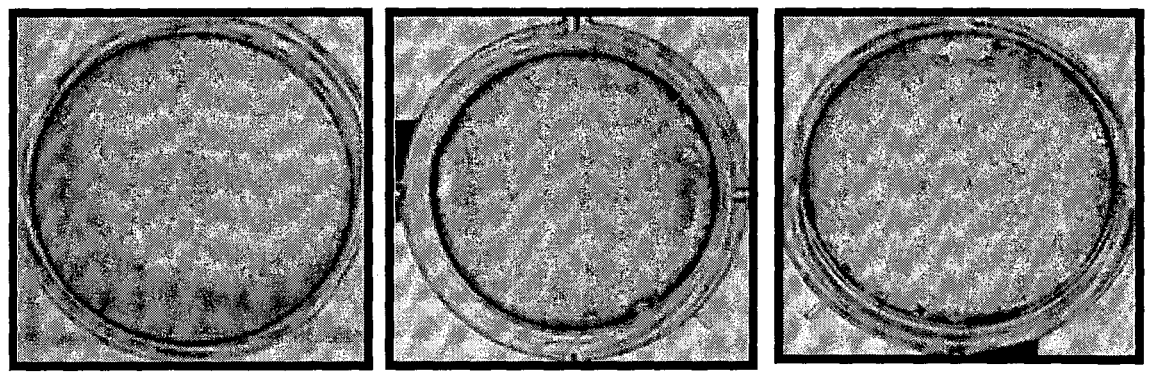
Figure 3:
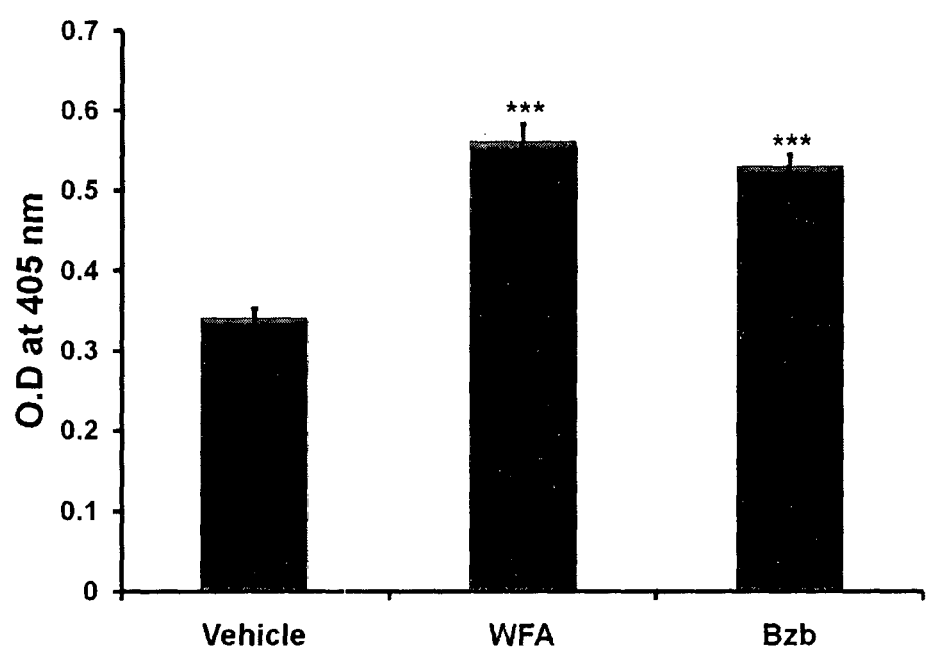

FIG. 3: Photomicrographs show that treatment of MCO's with WFA in osteoblast differentiation medium significantly increased mineralized nodules compared with control, as assessed by alizarin Red S staining. Quantitation of mineralization (Alizarin Red S stain) data is shown as O. D at 405 nm. Values represent Mean±S. E—of three independent experiments (n=3)***p<0.001 compared with control vehicle group.

Figure 4I:
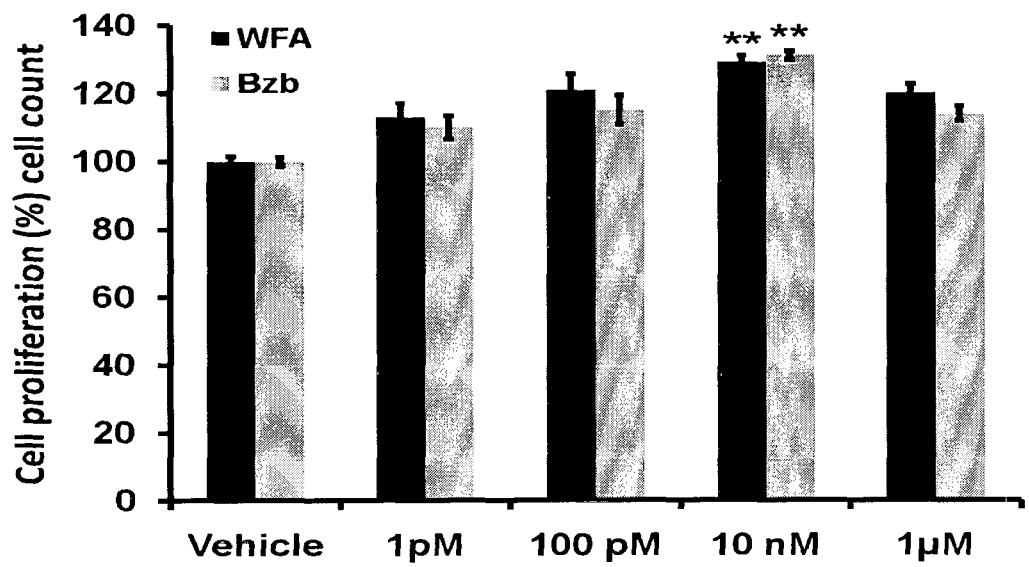
Figure 4:
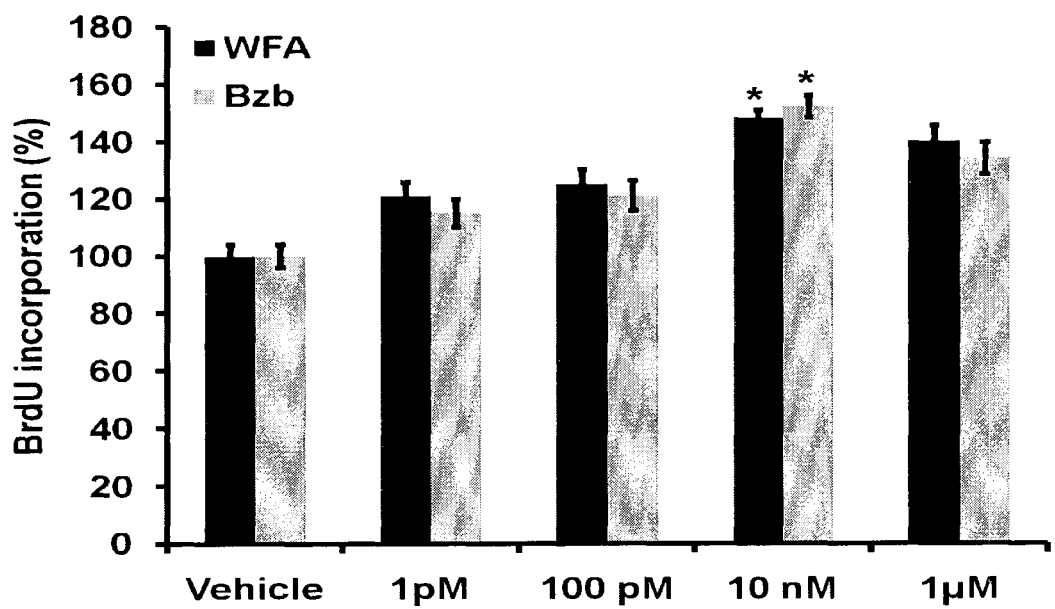

FIG. 4: Effect of WFA on primary osteoblast proliferation. Primary osteoblasts were cultured in increasing concentrations of WFA and Bzb for 24 h and harvested for cell proliferation Direct cell count for cell proliferation assay (i) and BrdU incorporation cell proliferation assay (ii). The results were expressed as relative cell growth in percentage, which was compared with control group. We set the control group as 100. Values represents Mean±S. E of three independent experiments (n=3). *p<0.05, **p<0.01 when compared with control.

Figure 5:
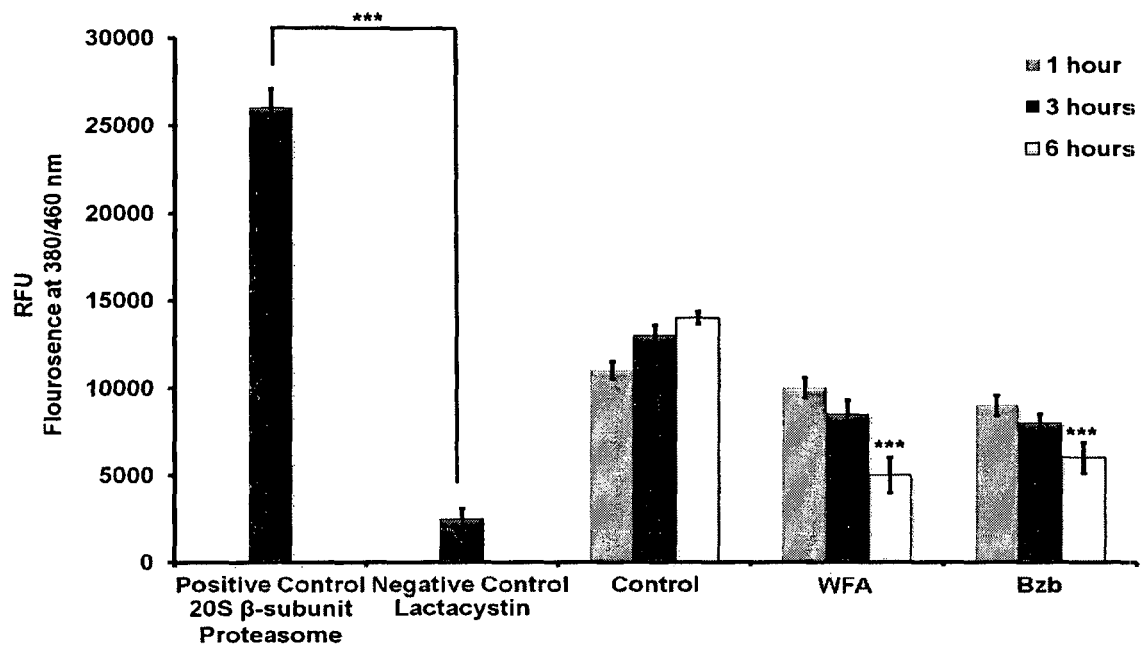

FIG. 5: Proteasomal effect of WFA in calvarial osteoblast cells. 20 S proteasome activities were measured 1, 3, 6 h after treatment with WFA. Values represent Mean±S. E of three (n=3) independent experiments ***p<0.001,*p<0.001 compared with control.

Figure 6:
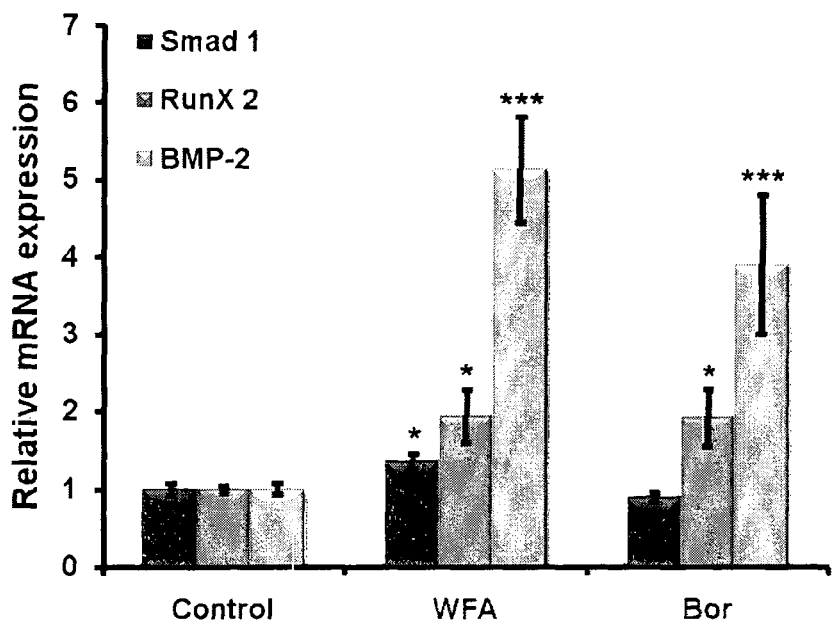

FIG. 6: WFA (10 nM) treatment of MCO's increased expression of osteogenic genes. Figure shows increased expression of RunX2, OCN and Col I with WFA treatment. Expression was normalized to GAPDH internal control. Values represent Mean±S. E of three independent experiments (n=3). *p<0.05,***p<0.001 compared with vehicle control group.

Figure 7:
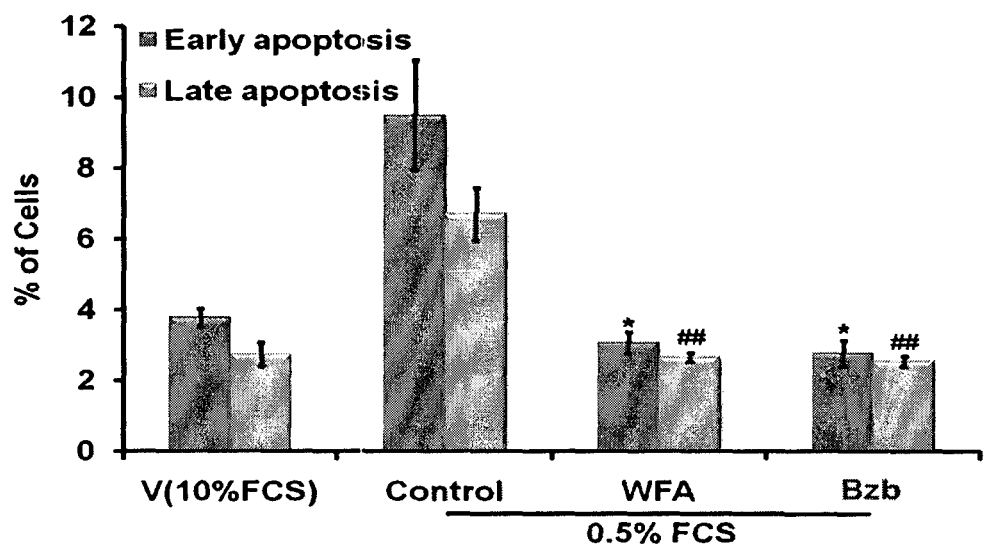

FIG. 7: Quantification of flow cytometry data is shown as percent of total cells. Values represents Mean±S. E of three independent experiments (n=3). *p<0.05 Compared with control for early apoptosis and ##p<0.01 compared with control for late apoptosis.

Figure 8:
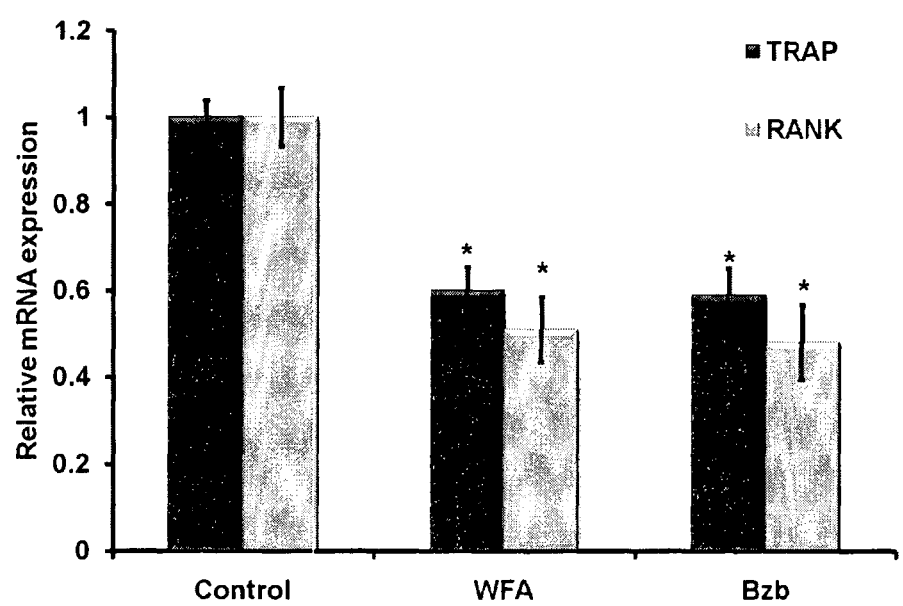

FIG. 8: WFA decreases mRNA levels of TRAP and RANK in osteoclast culture. BMCs were isolated from 4 to 6-weekold mice. After overnight culture cells were cultured for 6 days in the presence of MCSF and RANKL. mRNA levels of TRAP and RANK related to osteoclastogenesis was determined by qPCR from the total RNA made from BMC's. Data represent mean±SEM; n=3.P<0.01 and *P<0.001 compared to vehicle treated cells.

Figure 9:
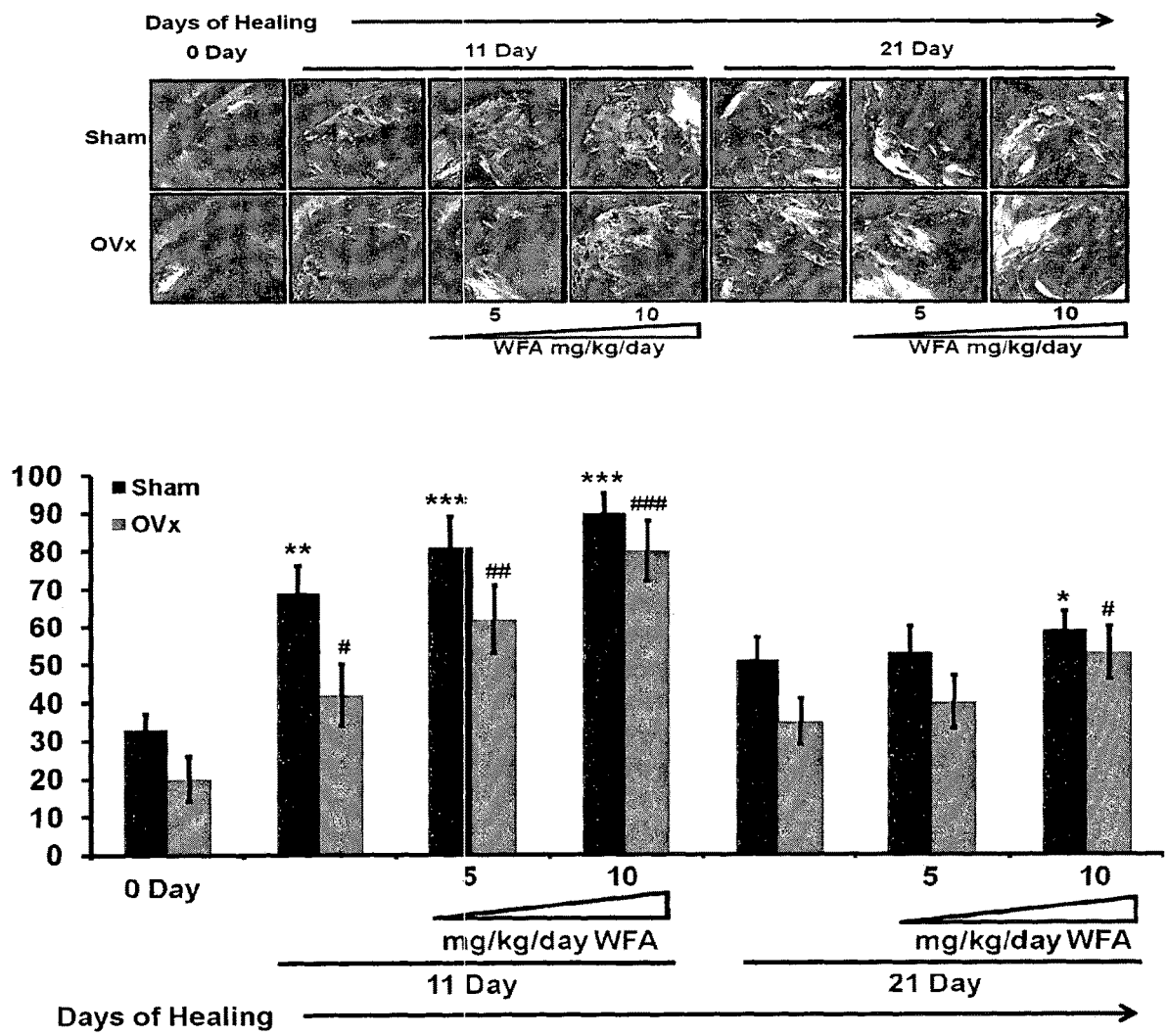

FIG. 9: Representative confocal images (magnification=100×) of calcein labeling shown in the drill hole site of various groups 0, 11 and 21 days after injury without and with WFA treatment(5 and 10 mg.kg$^{-1}$day$^{-1}$). Data shows the quantification of the mean intensity of calcein labeling. Values represent Mean±S. E p<0.01, *p<0.001 compared with Sham vehicle. #p<0.05##p<0.01, ###p<0.001 compared with OVx vehicle group. Interdose comparison shows that $^c$p<0.05 when 10 mg·kg$^{-1}$day$^{-1}$ dose was compared with 5mg·kg$^{-1}$day$^{-1}$ dose. *p<0.05 when OVx+V compared with Sham+V.

Figure 10:
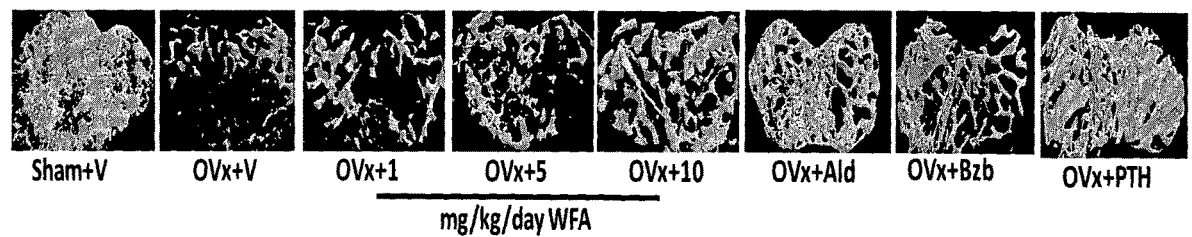

FIG. 10: WFA supplementation restores the trabecular microarchitecture of the femur epiphysis. Representative μCT images of the femur epiphysis of various experimental groups. μCT analysis of various trabecular parameters of the femur epiphysis, including BV/TV and SMI are presented. All values are expressed as mean±SEM *p<0.05, p<0.01, *p<0.001$^a$p<0.001 when 10 mg·kg$^{-1}$day$^{-1}$ dose compared with 1 mg·kg$^{-1}$day$^{-1}$ FIG. 11: WFA is devoid of uterine estrogenicity. Uteri were harvested from mice after various treatments Sham+V, OVx+V, OVx+1 mg$^{-1}$·day$^{-1}$, OVx+5 mg$^{-1}$·kg$^{-1}$. day$^{-1}$, OVx+10 mg$^{-1}$·kg$^{-1}$·day$^{-1}$, OVx+Ald, OVx+Bzb, OVx+PTH. Representative photomicrographs of the stained (H&E,4×) cross sections of the uteri. Histomorphometric calculations per-formed on these sections shown in table below.

Figure 12:
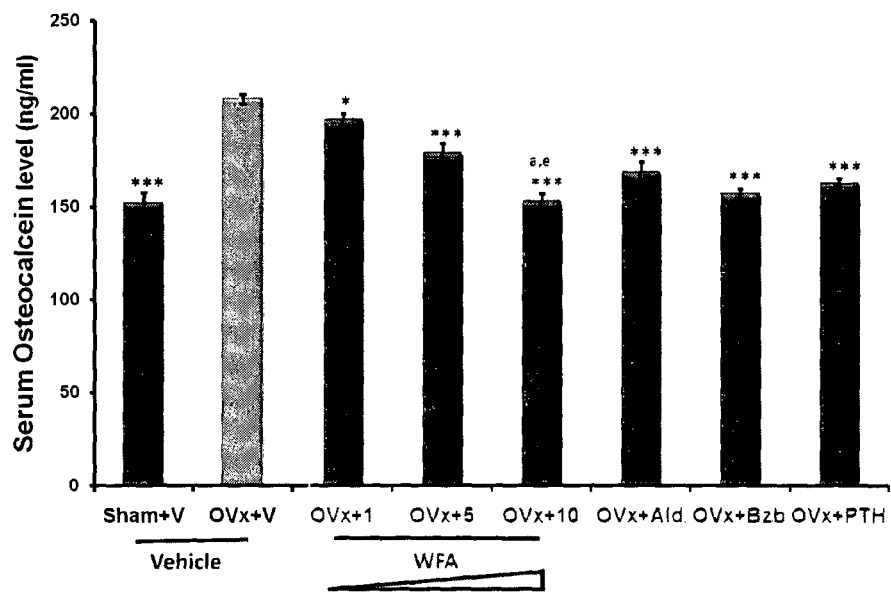

FIG. 12: Serum osteocalcin levels as measured at the end of experiment from various treatment groups. Data shows that WFA inhibits bone turnover in OVx mice. All values are expressed as mean±SEM *p<0.05, p–0.01, *p<0.001 compared with OVx group. $^a$p<0.001 when 10 mg·kg$^{-1}$day$^{-1}$ dose was compared with 1 mg·kg$^{-1}$day$^{-1}$ dose, $^e$p<0.01 when 10 mg·kg$^{-1}$day$^{-1}$ dose compared with 5 mg·kg$^{-1}$day$^{-1}$ dose.

Figure 13:
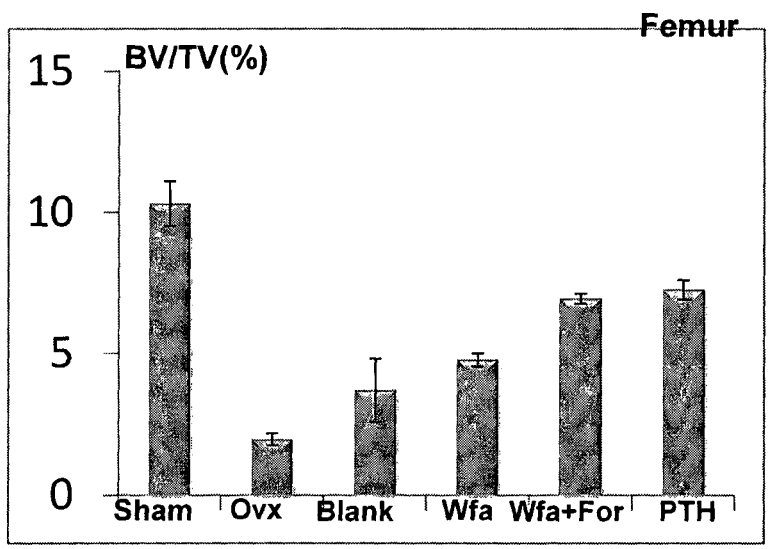

FIG. 13: Formulated kaempferol maintains trabecular micro-architecture after the treatment. μCT analysis of various trabecular parameter BV/TV of femur, are expressed as mean±SEM (n=12 rats/group).

Figure 14:
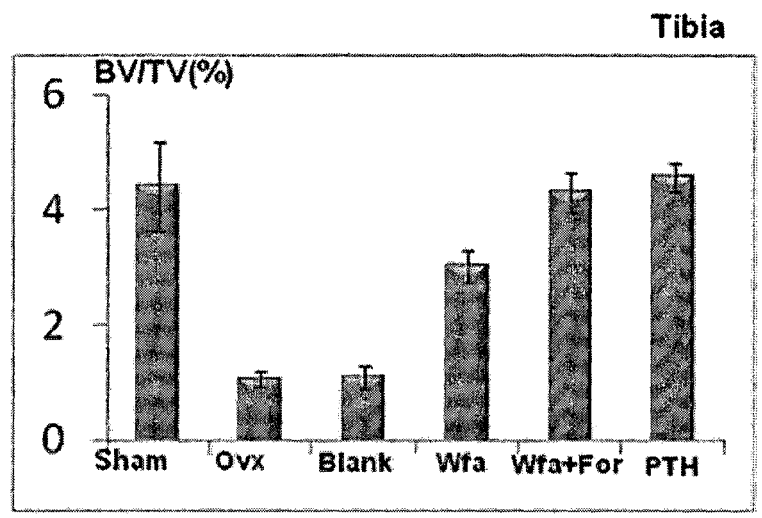

FIG. 14: Formulated kaempferol maintains trabecular micro-architecture after the treatment. μCT analysis of various trabecular parameters BV/TV of tibia, are expressed as mean±SEM (n=12 rats/group).

Figure 15:
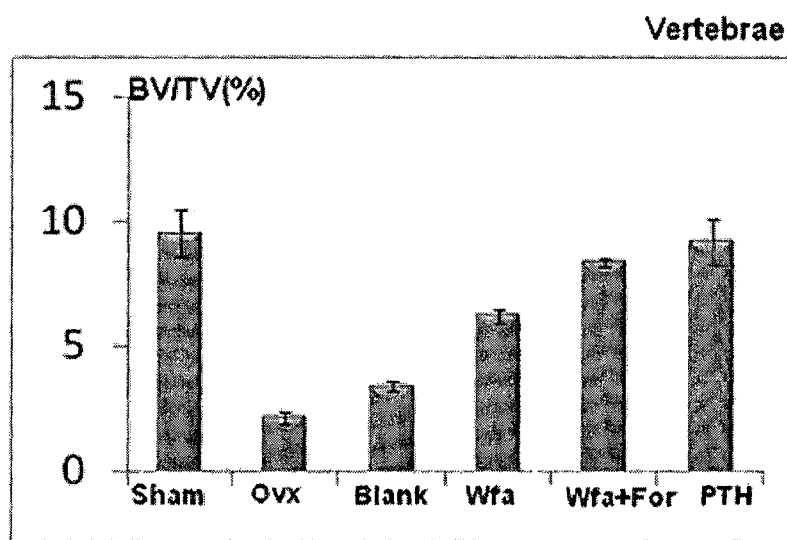

FIG. 15: Formulated kaempferol improved micro-architecture of vertebral trabeculae after the treatment. μCT analysis of trabecular parameter BV/TV. All values are expressed as mean±SEM (n=12 rats/group).

DETAILED DESCRIPTION OF THE INVENTION

The present invention relates to Withaferin A, a proteasomal inhibitor and its use in osteogenic activity, and pharmaceutical composition thereof. The present invention also relates to a pharmaceutical composition comprising the pure compound (Withaferin A) isolated from plants that is useful for the prevention and/or treatment of medical conditions associated with estrogen dependent or independent diseases or syndromes, preferably in the prevention or treatment of diminution of bone tissue in humans and animals, and achievement of peak bone mass and bone health during skeletal growth.

More particularly, the present invention relates to the use of biologically isolated pure compound, Withaferin A, as the representative case from *Withania somnifera* plant from the family *Solanaceae*, and their pharmaceutically acceptable compositions.

The core of the present invention is a novel pharmaceutical composition comprising Withaferin A for the prevention and treatment of osteoporosis and related fractures with respect to:
 (a) disclosure of pharmacological activity of curing and recovery from OVx induced osteoporosis;
 (b) disclosure of composition of the extract defined in molecular form;
 (c) exhibition of distinct treatment of OVx induced osteoporosis because of presence of Withanolides (Withaferin A, Withanone and Withanolide A) which have so far not been reported for such activity.

No natural proteasome inhibitor has been reported to demonstrate enhanced osteogenic effect. However, the present invention on the anti-osteoporotic activity of Withanolides in vivo as shown in estrogen deficient model in rat clearly demonstrates the therapeutic efficacy of said Withanolides in treating mammals after osteoporosis and fractures. Therefore, the present invention describing the anti-osteoporic activity of Withanolides has novelty. The present invention relates to the demonstration and disclosure of anti-osteoporotic activity of Withanolides: Withaferin A, Withanone and Withanolide A as the representative cases. Withanolides (Withanolide A and Withanone) can be extracted from plants belonging to the Solanaceae family, selected form any of its genera or species.

The main embodiment of the invention is the use of Withaferin A, Withanolides, and Withanolide A for osteogenic action.

The main embodiment of the invention is the use of Withanolides; Withanolide A, Withaferin A, or Withanone, or a preparation containing Withaferin A for the treatment of osteoporosis and related fractures in mammals.

Even further embodiment of the invention is a pharmaceutical composition wherein the bioactive Withaferin A, Withanolide A, or Withanone is in pure form.

Further embodiment of the present invention is to provide a proof of the principle that Withaferin A functions as proteasomal inhibitor responsible for increasing osteoblast proliferation.

Even further embodiment of the invention is that the Withaferin A increases mineralization of osteoblasts cells.

Yet another embodiment of the invention is to increase the absorption of Withaferin A using pharmaceutical composition.

Further embodiment of the invention is the pharmaceutical preparations wherein the bioactive is Withaferin A.

Another embodiment of the invention is the pharmaceutical preparation wherein the Withaferin A, and Withanolides (Withanolide A or Withanone) may be present separately.

Yet another embodiment of the invention is the addition of pharmaceutically acceptable excipients including but not limited to, the group consisting of chitosan, lecithin, cholesterol, gum arabic, starches, guar gum, lecithin, cholesterol, sorbates, lactose [GRAS category]. The excipients selected are biocompatible and biodegradable in nature.

The formulation comprises of Soya lecithin, DSPC and cholesterol in molar ratio of 7:3:3. The coating of chitosan (0.2% w/v) was provided to render mucoadhesive property, as well as to enhance the stability of liposomes at gastric pH. The chitosan coating provides a unique advantage in delivering withaferin A through oral route and provides comparable effect to parathyroid hormone (PTH).

Yet another embodiment of the invention is to compare withaferin A bearing pharmaceutical composition for osteogenic efficacy with Bzb (Bortizomib) which is a synthetic proteasomal inhibitor used in multiple myeloma therapy.

Pharmaceutical formulations of the present invention may be administered through various routes of administration. For example, formulations may be administered orally and through parenteral route.

Even further embodiment of the invention is the pharmaceutical preparation may be in any physical form such as suspension, powder, injectable, syrup, capsules, tablets or controlled release formulation etc.

The pharmaceutical composition containing withaferin A of the present invention wherein the diminution of bone tissue may be prevented caused due to estrogen loss, aging, arthiritis and drug induction.

EXAMPLES

The invention is described by way of illustrative examples. The examples or the accompanying drawings should not be construed to limit the scope of the invention to the accompanying drawings.

WFA was purified from *Withania somnifera* grown and collected from CSIR-Central Institute of Medicinal and Aromatic Plants, Lucknow, Uttar Pradesh, India.

Example 1

Isolation of Withanolide A and Withanone and Withaferin:

Withanolide A and Withanone were isolated from *Withania somnifera* by column chromatography, followed by crystallization, followed by recrystallization, and subjected to various spectral analyses including IR, mass-spectrometry, and NMR for final structural assignment of Withanolide A and Withanone, as reported by us (Misra et al., Phytochemistry 66: 2702-2707, 2005; Sangwan et al., Chemical and Pharmaceutical Bulletin 55: 1371-1375, 2007; Misra et al., Phytochemistry 69: 1000-1004, 2008;).

For each in-vitro experiment, Mice Calvarial osteoblasts (MCOs) were procured from 1 to 2day old mice pups. For cells, 20 to 35 calvaria were harvested from pups at room temperature (25° C.). Briefly, individual calvaria were surgically isolated from the skull, the sutures were segregated, and the adherent tissue material was cleaned by gentle scrapping. The pooled calvarias were kept for repeated digestion (15 minutes/digestion) with 0.1% dispase and 0.1% collagenase P to release the cells. First digestion was discarded and cells were collected from next four digestions. These cells were cultured in a modified essential medium (a-MEM) containing 10% fetal calf serum (FCS) and 1% penicillin/streptomycin (complete growth medium). Cultures of MCO's were allowed to reach 80% confluence for the experiments.

Example 2

Mice Calvarial Osteoblast (MCO) Culture

For each experiment, 1 to 2 day old MCOs were used to harvest 20 to 35 calvaria at room temperature (25° C.). Briefly, individual calvaria were surgically isolated from the skull, the sutures were segregated, and the adherent tissue material was cleaned by gentle scrapping. As described previously, the pooled calvarias were kept for repeated digestion (15 minutes/digestion) with 0.05% trypsin and 0.1% collagenase P to release the cells. First digestion was discarded and cells were collected from the next four digestions. These cells were cultured in a modified essential medium (a-MEM) containing 10% fetal calf serum (FCS) and 1% penicillin/streptomycin (complete growth medium). Cultures of MCOs were allowed to reach 80% confluence for the experiments.

Alkaline Phosphatase (ALP) and Mineralization Assay for Withanolides and Bortizomib For the measurement of ALP activity, MCOs at approximately 80% confluence were trypsinized, and $2\times10^3$ cells/well were seeded onto 96-well plates. The cells were treated with withaferin A (WFA), withanolide (WNA) A, and withanone (WN) at different concentrations (1 pM, 100 pM, 10 nM, 1 µM) or vehicle for 48 h in α-MEM supplemented with 10% FBS, 10 mM β-glycerophosphate, 50 mg·mL$^{-1}$ of ascorbic acid, and 1% penicillin/streptomycin (osteoblast differentiation medium). At the end of incubation period, total ALP activity was measured using p-nitrophenylphosphate (PNPP) as substrate, and absorbance was read at 405 nm.

Mineralization assay was carried out to assess the mineralizing ability and thus bone formation of osteoblasts cells. For this MCOs were seeded onto 12-well plates (25,000 cells/well) in osteoblast differentiation medium with or without WFA (10 nM) and Bzb (10 nM) for 21 days with a medium change every 48 h. At the end of the experiment, the cells were washed with PBS and fixed with paraformaldehyde (4%) in PBS for 15 minutes. Alizarin red-S stain was used for staining mineralized nodules, followed by extraction of the stain using 10% acetic acid and 10% ammonium hydroxide for colorimetric quantification at 405 nm.

Results: Data for MCOs at 80% confluence from 1 to 2 day old rats when treated with WFA, WNA, and WN at dose ranging from 1pM to 1 μM and stimulated ALP activity (FIG. 1) shows that dose of 10 nM was most effective in stimulating ALP activity for WFA, WNA, and WN. Whereas as WN did not stimulate ALP activity significantly compared to vehicle control FIG. 1(i) At same concentration WFA, WNA, WN stimulated mRNA expression of collagen I suggesting the proliferative and mineralization of the withanolides as shown in FIG. 1(ii).

The ALP activity of Withaferin-A was ~3 fold higher as compared to Bortizomib at 10 nM concentrations as shown in FIG. 2.

WFA stimulated mineralization (ability to lay newly formed calcium nodules) in MCOs. Quantitation of mineralization by extracting Alizarin-S dye shows significant increase in mineralization with WFA treatment as compared to control group. The stimulation was comparable to Bzb treatment (FIG. 3).

Example 3

Cell Proliferation Assay

To assess the proliferative ability of the osteoblast cells in the presence of Withaferin A, a cell proliferation was done by direct cell count and BrdU assay. Mice primary osteoblast cells were plated at a density of $2.5 \times 10^5$ cells/ml/well in 12 well plates at 37° C. After overnight incubation, the cells were treated with or without WFA and Bzb at a concentration of 10 nM for 24 h. The cells were trypsinized and viable cells were counted with a hemocytometer using trypan blue dye exclusion. Cell counts were performed in duplicate and repeated in three cultures. For bromodeoxy uridine (BrdU) cell proliferation assay MCOs at 80% confluence (FBS) were exposed with various concentrations (100-pM to 1-μM) of WFA and Bzb for 24 h. Cell proliferation was determined using BrdU ELISA (from Calbiochem, Darmstadt, Germany) using manufacturer's instructions. For the last 3h of the 24 h stimulation, the, cells were trypsinized and 2000 cells/well were seeded in a-MEM supplemented with 10% fetal bovine serum, and the cells were pulsed with BrdU. Absorbance at dual wavelength of 450-540 nm was measured with a microplate reader.

Results: WFA concentration dependently stimulated osteoblast proliferation was assessed by direct cell count (FIG. 4(i) and BrdU incorporation assay FIG. 4(ii) at the end of the experiment. Changes in cell count were calculated as compared with the control vehicle group that was set as 100. 10 nM concentration of WFA maximally stimulated MCO proliferation suggesting increased pool of proliferating osteoblast cells in the presence of WFA.

Example 4

20 S Proteasome Activity Assay

Cells ($2.0$-$4.0 \times 10^3$) were plated in each well of a 96-well plate and treated with either WFA or Bzb at different time intervals (1, 3 and 6 h) at 10 nM concentration. Lysate at different time intervals was collected using the manufacture's protocol, (*Proteasome* Activity Assay Kit, CHEMICON's). The assay is based on detection of the fluorophore 7-Amino-4-methylcoumarin (AMC) after cleavage from the labeled substrate LLVY-AMC. Free AMC fluorescence can be quantified using a 380/460 nm filter set in a fluorometer. Purified 20S proteasome subunit has been used as a positive control and a proteasome inhibitor, Lactacystin, is included as a test inhibitor (control) for screening purpose.

Results: As WFA has been reported to be a proteasomal inhibitor in prostate cancer cells (Chiang et al., Grover et al.), we investigated WFA's proteasomal effect in calvarial osteoblast cells. Proteasome activity of WFA on 20S subunit shows that WFA acts as a natural proteasome inhibitor in primary osteoblast cells (FIG. 5). Similar to Bzb, kinetic study showed that WFA inhibited proteasomal 20 S subunit activity as early as 3 h with maximum inhibition being at 6 h by ~40-50 percent as compared with the positive control. This inhibition was comparable to Bzb. Lactacystin, was used as a negative control that significantly inhibits the 20 S proteasomal activity. Data suggests that WFA is an effective naturally occurring proteasomal inhibitor in osteoblast cells.

Example 5

Quantitative Real Time PCR (Q-PCR)

Cells were homogenized using 1 ml of TRIzol reagent (Invitrogen, Carlsbad, Calif., USA), and total RNA was extracted according to the manufacturer's protocol. cDNA was synthesized using RevertAid™ First Strand cDNA synthesis kit (#K1621 Fermentas, Canada) from 1 μg of total RNA. Quantitative real time PCR amplifications were performed in The LightCycler® 480 Real-Time PCR System (Roche Diagnostics, USA) using LightCycler SYBR Green (Roche Diagnostics, USA) according to the manufacturer's instruction. The sequences of primer sets for Smurf1, Smurf2, RunX2, BMP-2, alkaline phosphatase (ALP), osteocalcin (OCN), Collagen I (Coll) and GAPDH mRNAs, target sites on mRNAs and product sizes by PCR are shown in FIG. 6. The quantity of each sample was normalized using the CT (threshold cycle) value obtained for the GAPDH mRNA amplifications.

Results: WFA at 10 nM treatment of MCOs increased expression of osteogenic genes. FIG. 9 shows increased expression of RunX2, OCN and Col I with WFA treatment. Expression was normalized to GAPDH internal control. Values represent Mean±S. E of three independent experiments (n=3). *p<0.05, *** p<0.001 compared with vehicle control group (FIG. 6). From this data it can be concluded that WFA increases expression of mineralizing genes and thus mineralization of osteoblast.

Example 6

Apoptosis Assay

Mice calverial osteoblast were grown to 50% to 60% confluence, followed by serum withdrawal for 3 h and treatment with WFA (10 nM) and Bzb (10 nM) or without treatment for 24 h in a-MEM containing 0.5% FBS. Annexin V/PI staining for fluorescence-activated cell sorting (FACS) analysis was carried out using Calbiochem Annexin V-FITC Apoptosis Detection Kit (Calbiochem, USA) according to manufacturer's instructions.

Results: To study whether apoptosis was induced in MCOs by serum deprivation (0.5% FBS containing medium), and the effect of WFA was analyzed by FACS following annexin V/PI staining. MCOs cultured in 10% FBS contained 4% total apoptotic cells (early and late apoptotic cells) compared with ~8% under apoptotic (0.5% FBS) conditions. When WFA was added to serum deprived MCO cultures, only 3% of the cells were found to be apoptotic. Data was comparable to standard control Bortizomib (Bzb) (FIG. 7). Therefore, it can be concluded that WFA inhibited osteoblastic apoptosis to increase bone formation.

Example 7

Osteoclast Culture and Real-time Expression of TRAP and RANK

In vitro osteoclastogenesis was performed using standard protocol. Mouse bone marrow cells were flushed from femur using alpha-MEM. Cells were seeded in flask overnight in Osteoclast medium (alpha MEM, 10% FCS, antibiotic, EBSS, 10 ng/ml MCSF). After overnight incubation, non-adherent bone marrow cells were seeded in 48-well plates at a density of 2,00,000cells/well and cultured for 5-6 days in alpha-MEM containing 10% FCS, EBSS, 50 ng/ml RANKL, 10 ng/ml MCSF and WFA, and Bzb at different concentrations. The medium was replaced after every 48 hours. After 6 days of culture, the cells were washed with PBS and then fixed in 4% paraformaldehyde or used for RNA extraction using TRIZOL for analysis of TRAP, RANK mRNA levels by real-time PCR. Fixed cells were followed by TRAP staining using the standardized protocol.

Results: The expression of osteoclastogenic genes, TRAP and RANK were assessed in bone marrow cultures. FIG. 8 shows that WFA treatment significantly reduced mRNA levels of TRAP and RANK compared with control vehicle. Overall, the data suggests that in addition to direct effect of WFA in inhibiting osteoclast differentiation, it also inhibits osteoblast-generated osteoclastogenesis.

Example 8

Fracture Healing Drill-hole Study

Sixty adult Balb/c mice (18-20 g each) were taken and divided into six groups of three each for the study. Each group included 12 animals per group. First three groups of Sham (ovary intact) include (Sham+V, Sham+5 mg.kg$^{-1}$ of WFA, Sham+10 mg·kg$^{-1}$day$^{-1}$ of WFA) and the other 3 groups with OVx (bilateral ovariectomy include OVx+V, OVx+5 mg·kg$^{-1}$day$^{-1}$, OVx+10 mg·kg$^{-1}$day$^{-1}$ of WFA). Mice were left for 8 weeks for the OVx mice to develop osteopenia. After 8 weeks, drill-hole injury was created in both sham and OVx groups. In mid femur region the front skin was incised straight and longitudinally 1 cm in length under anesthetic condition. After splitting the muscle, periosteum was stripped to expose the femoral bone surface. A drill-hole injury was made, 1 cm above the knee joint by inserting a drill bit with a diameter of 0.1 mm in the anterior portion of the diaphysis of the bilateral femurs. Treatment of WFA started from the next day of injury and continued for 21 days. Each animal received intraperitoneal administration of fluorochrome calcein (20 mg·kg$^{-1}$) 24 h before autopsy. After 21 days of treatment as described above, all mice were euthanized and autopsied to collect their femurs for the measurement of bone micro architectural parameters at the drill hole site. Bones were embedded in acrylic material and 50 μm sections were made using an Isomet BoneCutter (Buehler, Lake Bluff, Ill. USA) and photographs were taken under confocal microscope LSM 510 Meta, Carl Zeiss, USA) aided with appropriate filters. The intensity of calcein binding, which is an indicator of the amount of new mineral deposition, was calculated using Carl Zeiss A M 4.2 image-analysis software.

Results: To verify the direct action of WFA on osteoblast differentiation and bone formation by observation of regenerating bone in the drill hole, we monitored the local repair process using μ-CT from days 11 to 21 after creation of the drill hole in vivo (He et al, Nagashima et al, 2005; Sharan et al, Tanaka et al). Data shows that WFA treatment at both doses of 5 and 10 mgkg$^{-1}$d$^{-1}$ increased mineral deposition (measured from the intensity of calcein labeling in the drill hole) as compared with controls, mice receiving vehicle only (FIG. 9).

In OVx and Sham groups, modest mineralized calluses appeared at both defect region and intramedulla region. At day 11, the extent of callus mineralization had increased, even in the intramedulla region. After day 11 post drilling, WFA treatment at 5 mg kg$^{-1}$d$^{-1}$ dose led to predominantly occupied mineralized callus, and the defect region was partially bridged. As compared with the 5 mg kg$^{-1}$d$^{-1}$, 10 mgkg$^{-1}$ d$^{-1}$ had more significant effect with more increased mineralized callus within the intra medulla region to be remodeled to completely bridge the defect (FIG. 10). In OVx mice extent of mineralization was assessed 6 weeks post surgery, OVx mice had significantly lower mineral deposition (50% less) than the sham+vehicle group. However, WFA at both the doses (5 and 10 mg kg$^{-1}$d$^{-1}$) increased mineral deposition in OVx mice compared with OVx mice treated with vehicle (FIG. 9).

Example 9

In Vivo Eficacy Studies of WFA on Ovariectomized (OVx) Mice

Eighty adult Balb/c mice (18-20 g each) were randomly divided into eight equal groups as follows: sham operated (ovary intact), vehicle (gum acacia in distilled water), OVx vehicle, OVx+40 μg·kg$^{-1}$ of injectable parathyroid hormone (iPTH; 3 days/week), OVx+3 mg·kg$^{-1}$day$^{-1}$ of Alendronate (Aln), OVx+1.0 mg·kg$^{-1}$day$^{-1}$ of WFA, OVx+5.0 mg·kg$^{-1}$ of WFA, OVx+10.0 mg·kg$^{-1}$day$^{-1}$ of WFA, OVx+0.3 mg·kg$^{-1}$day$^{-1}$ of Bzb. The intraperitoneal dose for iPTH (40 μg·kg$^{-1}$ for 3 days/week) used in this study as known anabolic agent. The possible role of various treatments (WFA, Bzb) was assessed in estrogen deficient bone loss model for 8 weeks post ovariectomy .The above mentioned various treatments started 8 weeks after the surgery and continued for 8 weeks. For dynamic histomorphometry measurements each animal was administered intraperitoneally with fluorochromes tetracycline (20 mg·kg$^{-1}$) on day 30 (1 week) and calcein (20 mg·kg$^{-1}$) on day 60 (8 weeks) after the commencement of various treatments. After 8 weeks of treatment, all mice were euthanized and autopsied to collect bones (i.e., tibias and femurs) for measurement of bone parameter. BMCs from tibias and femurs of vehicle- or WFA-treated mice were harvested, and mineralization was studied as described previously. BMCs were cultured in bone marrow differentiation medium to induce mineralization for 18 days. Mineralization was quantified as described. Alizarin red S stain was used for staining mineralized nodules, followed by extraction of the stain for quantification. For pharmacokinetic analysis the blood samples were withdrawn at various time intervals (0, 0/25, 0.5, 1, 2, 3, 4, 5, 8, 24 hrs) after oral administration of WFA at the dose of 10 mg·kg$^{-1}$. The plasma samples were analyzed by HPLC according to reported method with slight modification.

Microcomputed Tomography (μCT)

Sky Scan 1076 μCT scanner (Aartselaar, Belgium) was used to carryout μCT scanning of excised bones as described before. The bone samples were scanned at a resolution of 9 μm and reconstruction was done using the Sky Scan Nrecon software. The X-ray source was set at 50 kV and 200 mA, with a pixel size of 9 μm. A hundred projections were acquired over an angul arrange of 180°. CTanalyser (CTAn, Skyscan) software was used to draw ellipsoid contours in selected trabecular bone. Mean intercept length method was used to calculate trabecular bone volume, trabecular number (Tb.N), and trabecular separation (Tb.Sp) of the distal femoral epiphysis (covering secondary spongiosa and the secondary ossification center) and proximal tibial metaphysis. Trabecular thickness (Tb.Th) and structure mode index (SMI) was calculated according to the method of Hildebrand and Ruegsegger. 3D parameters were based on analysis of a Marchingcubes-type model with a rendered surface. CT Vol software was used to create 3D model of the bones.

Results: Trabecular response to WFA treatment to ovariectomized rats was quantified at the tibia proximal (FIG. 13) Tibial data shows that compared with sham operated group, the OVx+vehicle group exhibited significantly reduced BV/TV. Treatment with WFA reversed these deleterious effects on bone. No significant difference in BV/TV was observed as compared to sham operated group. Interdose comparison of WFA treatment with sham control group revealed that out of the three doses of 1, 5 and 10 mg kg$^{-1}$day$^{-1}$, 10 mg kg$^{-1}$day$^{-1}$ dose was the most effective dose (FIG. 10).

Example 10

Estrogenicity Studies of WFA

The uterus of each mouse was weighed and then fixed in 4% paraformaldehyde. A middle segment of each uterus was dehydrated in ascending grades of isopropanol, cleared in xylene and sections of about 5 μm thickness was prepared. Haematoxylin and eosin staining was done of 5 μm transverse sections and representative images were captured. Leica Qwin-Semiautomatic Image Analysis software (Leica Microsystems GmbH) was used to measure total uterine area, luminal area and luminal epithelial height.

Results: Assessment of uterine weight was performed for estrogenecity. OVx results in decrease in uterine weight significantly compared to Sham (p<0.001,-4 fold) (FIG. 11). OVx results in decreases in uterine weight (p<0.001) but Withaferin A treatment at all doses show uterine weight comparable to OVx group eliminating possibility of endometrial hyperplasia.

Example 11

Effect of WFA on Bone Turnover Markers

Rat-MID™ Osteocalcin EIA (Immunodiagnostic, UK) performed using serum from treated and vehicle groups using manufacturer's protocol as provided in the kit.

Results: FIG. 12 shows that serum osteocalcin are significantly elevated in the OVx+vehicle group compared with sham+vehicle group. Treatment of WFA for 60 days to OVx mice result in significant reduction in the levels of OCN compared with OVx+vehicle group. This data suggests that WFA inhibits bone turnover that is characteristically elevated under estrogen deficiency.

Example 12

Chitosan coated liposomal formulation was developed using thin film hydration method. Liposomes were formulated using Distearoly Phosphatidylcholine (DSPC), Soya PC and cholesterol (7:3:3 moles). Lipids along with WFA (0.1% w/v) dissolved in chloroform and evaporated in rotavapour to form a thin film. The formed thin film was kept in vacuum for 12 hrs and hydrated with 10 ml PBS 7.4. Hydrated multilayered lipid vesicles were extruded sequentially through 400 nm, 200 nm and finally 100 nm filter for 15 cycles. GC coating was carried out by dispersing formulated liposomes in 0.2% GC solution for 10 min under stirring.

Results: Liposomes were collected by size exclusion chromatography and subjected to size and zeta potential analysis. Coating with GC was characterized by shift in zeta potential from −33.4 (±4.2) mV to +28.63 (±6.3) as well as increase in size of liposomes from 212(±6.2) nm to 276 (±12.39) nm. Percent entrapment efficiency (% EE) was determined by using gel filtration chromatography. 100 μl of Eluted liposomes was lysed with 900 μl methanol and after appropriate dilution analyzed by RP HPLC. The EE was found to be 92.63(±2.73)%. Oral administration of chitosan capped liposomal formulation with WFA to ovariectomized rats for three months restored bone volume/tissue volume (BV/TV) in femur (FIG. 13), in tibia (FIG. 14) and vertebrae (FIG. 15) compared to ovariectomized group by 76% and >than 25% as compared to free WFA group.

Example 13

Chitosan coated liposomal formulation was developed using thin film hydration method. Liposomes were formulated using DSPC, Soya PC and cholesterol (4:3:3 moles). Lipids along with WFA (0.2% w/v) dissolved in the mixture of ethanol and chloroform and evaporated in rotavapour to form a thin film. The formed thin film was kept in vacuum for 12 hrs and hydrated with 10 ml PBS 7.4. Hydrated multilayered lipid vesicles were extruded sequentially through 400 nm, 200 nm and finally 100 nm filter for 15 cycles. GC coating was carried out by dispersing formulated liposomes in 0.2% GC solution for 10 min under stirring.

Results: Liposomes were collected by size exclusion chromatography and subjected to size and zeta potential analysis. Coating with GC was characterized by shift in zeta potential from −34.2 (±3.8) mV to +30.82 (±4.8) as well as increase in size of liposomes from 220(±5.6) nm to 282 (±10.45) nm. Percent entrapment efficiency (% EE) was determined by using gel filtration chromatography. 100 μl of Eluted liposomes was lysed with 900 μl methanol and after appropriate dilution analyzed by RP HPLC. The EE was found to be 93.58(±3.5)%. Oral administration of chitosan capped liposomal formulation with WFA to ovariectomized rats for three months restored bone volume/tissue volume (BV/TV) compared to ovariectomized group by 76% and >than 25% as compared to free WFA group.

Example 14

Chitosan coated liposomal formulation was developed using thin film hydration method. Liposomes were formulated using DSPG, Soya PC and cholesterol (7:3:3 moles). Lipids along with WFA (0.3% w/v) dissolved in chloroform and evaporated in rotavapour to form a thin film. The formed thin film was kept in vacuum for 12 hrs and hydrated with 10 ml PBS 7.4. Hydrated multilayered lipid vesicles were extruded sequentially through 400 nm, 200 nm and finally 100 nm filter for 15 cycles. GC coating was carried out by dispersing formulated liposomes in 0.2% GC solution for 10 min under stirring.

Results: Liposomes were collected by size exclusion chromatography and subjected to size and zeta potential analysis. Coating with GC was characterized by shift in zeta potential from −31.4 (±3.8) mV to +30.53 (±5.2) as well as increase in size of liposomes from 225(±3.8) nm to 276 (±12.39) nm. Percent entrapment efficiency (% EE) was determined by using gel filtration chromatography. 100 μl of Eluted liposomes was lysed with 900 μl methanol and after appropriate dilution analyzed by RP HPLC. The EE was found to be 94.48(±4.6)%. Oral administration of chitosan capped liposomal formulation with WFA to ovariectomized rats for three months restored bone volume/tissue volume (BV/TV) compared to ovariectomized group by 76% and >than 25% as compared to free WFA group.

Example 15

Chitosan coated liposomal formulation was developed using thin film hydration method. Liposomes were formulated using DSPG, Soya PC and cholesterol (4:3:3 moles). Lipids along with WFA (0.5% w/v) dissolved in the mixture of ethanol and chloroform and evaporated in rotavapour to form a thin film. The formed thin film was kept in vacuum for 12 hrs and hydrated with 10 ml PBS 7.4. Hydrated multilayered lipid vesicles were extruded sequentially through 400 nm, 200 nm and finally 100 nm filter for 15 cycles. GC coating was carried out by dispersing formulated liposomes in 0.2% GC solution for 10 min under stirring.

Results: Liposomes were collected by size exclusion chromatography and subjected to size and zeta potential analysis. Coating with GC was characterized by shift in zeta potential from −28.4 (±3.2) mV to +27.57 (±4.3) as well as increase in size of liposomes from 228(±5.2) nm to 276 (±12.39) nm. Percent entrapment efficiency (% EE) was determined by using gel filtration chromatography. 100 μl of Eluted liposomes was lysed with 900 μl methanol and after appropriate dilution analyzed by RP HPLC. The EE was found to be 92.63(±2.73)%. Oral administration of chitosan capped liposomal formulation with WFA to ovariectomized rats for three months restored bone volume/tissue volume (BV/TV) compared to ovariectomized group by 76% and >than 25% as compared to free WFA group.

Example 16

Chitosan coated liposomal formulation was developed using thin film hydration method. Liposomes were formulated using Distearoly Phosphatidylcholine (DSPC), Soya PC and cholesterol (7:3:3 moles). Lipids along with Withanolide A (0.1% w/v) dissolved in the mixture of ethanol and chloroform and evaporated in rotavapour to form a thin film. The formed thin film was kept in vacuum for 12 hrs and hydrated with 10 ml PBS 7.4. Hydrated multilayered lipid vesicles were extruded sequentially through 400 nm, 200 nm and finally 100 nm filter for 15 cycles. GC coating was carried out by dispersing formulated liposomes in 0.2% GC solution for 10 min under stirring.

Results: Liposomes were collected by size exclusion chromatography and subjected to size and zeta potential analysis. Coating with GC was characterized by shift in zeta potential from −32.4 (±4.2) mV to +27.63 (±6.3) as well as increase in size of liposomes from 215(±6.2) nm to 273 (±12.39) nm. Percent entrapment efficiency (% EE) was determined by using gel filtration chromatography. 100 μl of Eluted liposomes was lysed with 900 μl methanol and after appropriate dilution analyzed by RP HPLC. The EE was found to be 89.42(±3.8)%. Oral administration of chitosan capped liposomal formulation with WFA to ovariectomized rats for three months restored bone volume/tissue volume (BV/TV) in femur, tibia and vertebrae compared to ovariectomized group by 74% and >than 22% as compared to free Withanolide A group.

Example 17

Chitosan coated liposomal formulation was developed using thin film hydration method. Liposomes were formulated using Distearoly Phosphatidylcholine (DSPC), Soya PC and cholesterol (7:3:3 moles). Lipids along with Withanone (0.1% w/v) dissolved in the mixture of ethanol and chloroform and evaporated in rotavapour to form a thin film. The formed thin film was kept in vacuum for 12 hrs and hydrated with 10 ml PBS 7.4. Hydrated multilayered lipid vesicles were extruded sequentially through 400 nm, 200 nm and finally 100 nm filter for 15 cycles. GC coating was carried out by dispersing formulated liposomes in 0.2% GC solution for 10 min under stirring.

Results: Liposomes were collected by size exclusion chromatography and subjected to size and zeta potential analysis. Coating with GC was characterized by shift in zeta potential from −30.6 (±3.8) mV to +25.43 (±4.2) as well as increase in size of liposomes from 212(±4.5) nm to 268 (±10.4) nm. Percent entrapment efficiency (% EE) was determined by using gel filtration chromatography. 100 μl of Eluted liposomes was lysed with 900 μl methanol and after appropriate dilution analyzed by RP HPLC. The EE was found to be 86.34(±4.3)%. Oral administration of chitosan capped liposomal formulation with WFA to ovariectomized rats for three months restored bone volume/tissue volume (BV/TV) in femur, tibia and vertebrae compared to ovariectomized group by 71% and >than 25% as compared to free Withanone group.

Example 18

Pharmacokinetic studies of chitosan coated liposomal formulation was carried out in Male Wistar rats. Male Wistar rats (body weight 200±20 g) were divided randomly into three groups of nine animals each. Rats were fasted for 2 h prior to the study. Equivalent amount (10mg/kg) of dissolved WFA, WFA/Lip and WFA/Lip-GC formulations were orally administered to each animal. 500 μl of blood was collected by retro-orbital puncture. Blood was centrifuged at 8,000 rpm for 10 min to isolate serum. WFA extraction and HPLC analysis was performed as described in our previous publication.

Results: The oral bioavailability of WFA loaded in chitosan coated liposomal formulation (WFA/Lip-GC) was determined and compared to free WFA suspended PBS. The plasma concentration-time profiles and resultant pharmacokinetic parameters of the plain WFA and coated Liposomes administered orally at dose of 10 mg/kg are presented in Table 2. Overall about 2.4 fold increased AUC was observed with coated liposomes. The increase might be attributed to sustain release behavior of GC coated Liposome which reduces free WFA in initial hrs. This higher bioavailability observed with liposomes can be attributed to the mucoadhesive property of chitosan and its ability to open tight junction of intestinal epithelial layers.

TABLE 2

Pharmacokinetic profile of Withaferin A and chitosan coated liposones

| PK parameters | WFA | WFA/Lip-GC |
|---|---|---|
| $C_{Max}$ (μg/ml) | 8.41 (±1.4) | 14.75 (±1.98) |
| $T_{max}$ (hrs) | 3 | 4 |
| AUC (hr * μg/ml) | 55.01 ± 8.4 | 132.18 (±21.6) |
| Vd (ml) | 0.043 | 0.897 |
| MRT (hrs) | 6.52 | 7.88 |

ADVANTAGES OF THE INVENTION

1. The major advantage of the formulation disclosed in the present invention lies in the fact that PTH is the only FDA approved molecule for osteogenic therapy available for the treatment of osteoporosis. However, it is very expensive and needs to be administered intravenously. There is also a report for black box warning of osteosarcoma reported in mice. The present invention provides a novel therapeutic use of withanolides (PI) for treatment of osteoporosis, an important health issue in humans, through oral route at much lower dose.

2. The present invention further provides and compositions based on Withanolides as potential novel drugs as proteasomal inhibitor (PI) for treatment of osteoporosis and related fractures and increase in bone length in pre-pubertal children.

3. The invention also provides a formulation comprising excipients with the Withanolides. The excipients are biodegradable and biocompatible and improve the absorption of Withaferin A.

4. The present invention further provides that withaferin A is orally effective for the postmenopausal osteoporosis.

5. The invention also provides a preparation comprising Withanolides, especially Withaferin A, which may be useful in achieving specific curative effect of osteoporosis which is comparable to PTH.

Abbreviations: Ald, Alendronate; ALP, Alkaline phasphatase activity; AUC, Area under the curve; BFR, Bone formation rate; BrdU, 5-Bromo-2'-deoxyuridine; Bzb, Bortezomib; BMCs, Bone Marrow Cells BMP2, Bone morphogenetic protein 2; BV/TV, Bone Volume/Tissue Volume; Col I, Collagen type I; EBSS, Earle's balanced salt solution; IL-6, Interleukin-6; MAR, Mineral apposition rate; MCO, Mouse calverial osteoblast; μ-CT Micro-computed tomography; iPTH, Injectible parathyroid hormone; MCP-1, Monocyte chemo-attractant protein-1; MRT, Mean residence time; NF-kB, nuclear factor kappa-B; OCN, Osteocalcin; OPG, Osteoprotegrin; OVx, Ovariectomy; PI, Proteasomal Inhibitor; PNPP, p-nitrophenylpyro-phosphate; Q-PCR, Quantitative Real Time PCR; RunX2, Runt related transcription factor 2; RANKL, Receptor activator of nuclear factor kappa-B ligand; RANK, Receptor activator of nuclear factor kappa-B; Smurf2, Smad ubiquitin regulatory factor; SMI, Structural Model Index; TRAP, Tartarate resistant acid phosphatase; Tb.No, Trabecular Number; Tb.Th, Trabecular Thickness; TNF-α, Tumor necrosis factor alpha; Vd, Volume of distribution; WFA, Withaferin A, DSPC-Distearoyl phoshatidylcholine, DSPG-Distearoyl phosphatidyl glycerol; GC, Glycol Chitosan.

We claim:

1. A method of treating diminution of bone tissue occurring due to osteoporosis, estrogen loss, aging, or drug induction, wherein the method comprises:
   administering to a subject in need thereof liposomes comprising Withaferin A in a concentration in the range of 0.1 to 0.5% w/v, glycol chitosan in a concentration in the range of 0.1 to 0.2% w/v, and distearoylphosphatidylcholine (DSPC), soya phosphatidylcholine (Soya PC), and cholesterol in the molar ratio of 7:3:3, wherein the liposomes are coated with the glycol chitosan; and
   wherein the liposomes induce osteogenic effect into mammalian bone tissue; and
   wherein the diminution of bone tissue is not caused by arthritis.

2. The method of treating diminution of bone tissue of claim 1, wherein the Withaferin A was obtained from *Withania Somnifera*.

3. The method of treating diminution of bone tissue of claim 1, wherein the liposomes comprise the Withaferin A in a concentration of 0.1% w/v.

4. The method of treating diminution of bone tissue of claim 1, wherein the liposomes are coated with the glycol chitosan in a concentration of 0.2% w/v.

5. The method of treating diminution of bone tissue of claim 1, wherein the liposomes comprise the Withaferin A in a concentration of 0.5% w/v.

6. The method of treating diminution of bone tissue of claim 1, wherein the liposomes additionally comprise a non-ionic surfactant.

7. The method of treating diminution of bone tissue of claim 6, wherein the non-ionic surfactant is selected from the group consisting of Tween-20, Tween-40, Tween-60, Tween-80, Span 40, Span 60, Span 80, and Cremophor.

8. A process for the preparation of the liposomes as claimed in claim 1, wherein the process comprises:
   (i) preparing a solution of the Withaferin A and the DSPC, Soya PC, and cholesterol in a solvent followed by evaporation of the solvent under reduced pressure to form a thin film;
   (ii) keeping the film obtained in (i) under vacuum up to 12 hrs and hydrating the film with PBS buffer at a pH in the range of 7.2 to 7.4 to obtain multilayered lipid vesicles;
   (iii) sequentially extruding the multilayered lipid vesicles obtained in (ii) through 400 nm, 200 nm, and 100 nm filter for 15 cycles to obtain a uniform population of vesicles;
   (iv) coating the uniform population of vesicles of (iii) with the 0.1 to 0.2% w/v glycol chitosan (GC) to obtain liposomes; and
   (v) dispersing the liposomes of (iv) in 0.2% w/v GC solution for 10 min under stirring to obtain a pharmaceutical composition.

9. The process as claimed in claim 8, wherein the solvent of (i) is selected from the group consisting of chloroform, ethanol, and mixture thereof.

10. The process for preparation of the liposomes as claimed in claim 8, wherein the Withaferin A was obtained from *Withania Somnifera*.

11. A method of treating diminution of bone tissue occurring due to osteoporosis, estrogen loss, aging, or drug induction, wherein the method comprises:
   administering to a subject in need thereof liposomes comprising Withaferin A in a concentration of 0.5% w/v, glycol chitosan in a concentration of 0.2% w/v, and distearoylphosphatidylcholine (DSPC), soya phosphatidylcholine (Soya PC), and cholesterol in the molar ratio of 7:3:3, wherein the liposomes are coated with the glycol chitosan; and
   wherein the liposomes induce osteogenic effect into mammalian bone tissue; and
   wherein the diminution of bone tissue is not caused by arthritis.

* * * * *